(12) United States Patent
Smith

(10) Patent No.: US 9,314,396 B2
(45) Date of Patent: *Apr. 19, 2016

(54) TRACTAL ERECTILE DEVICE AND SEAL CAP

(71) Applicant: Richard L. Smith, Macedonia, OH (US)

(72) Inventor: Richard L. Smith, Macedonia, OH (US)

(73) Assignee: Richard L. Smith, Macedonia, OH (US)

( * ) Notice: Subject to any disclaimer, the term of this patent is extended or adjusted under 35 U.S.C. 154(b) by 594 days.

This patent is subject to a terminal disclaimer.

(21) Appl. No.: 13/767,416

(22) Filed: Feb. 14, 2013

(65) Prior Publication Data

US 2013/0226054 A1 Aug. 29, 2013

Related U.S. Application Data

(60) Provisional application No. 61/602,316, filed on Feb. 23, 2012.

(51) Int. Cl.
*A61F 5/00* (2006.01)
*A61H 19/00* (2006.01)
*A61F 5/41* (2006.01)

(52) U.S. Cl.
CPC *A61H 19/32* (2013.01); *A61F 5/41* (2013.01); *A61F 2005/412* (2013.01)

(58) Field of Classification Search
CPC .............................. A61F 5/41; A61F 2005/411
USPC ...................................................... 600/38–41
See application file for complete search history.

(56) References Cited

U.S. PATENT DOCUMENTS

| | | | |
|---|---|---|---|
| 2,358,440 A | 9/1944 | Bowman | |
| 2,577,345 A | 12/1951 | McEwen | |
| 3,820,533 A | 6/1974 | Jones | |
| 4,175,554 A | 11/1979 | Gerow | |
| 4,640,270 A | 2/1987 | Chin | |
| 4,641,638 A | 2/1987 | Perry | |
| 4,671,262 A | 6/1987 | West | |
| 4,690,135 A | 9/1987 | Gerow | |
| 4,856,498 A | 8/1989 | Osbon | |
| 4,869,723 A | 9/1989 | Harmon | |
| 4,989,592 A | 2/1991 | Chang | |
| 5,213,563 A | 5/1993 | Cox | |
| 5,234,401 A | 8/1993 | Yamanaka | |
| 5,624,378 A | 4/1997 | Baldecchi | |
| 5,647,837 A | 7/1997 | McCarty | |
| 5,836,864 A | 11/1998 | Clark et al. | |
| 5,855,547 A | 1/1999 | Chaney | |
| 5,951,460 A | 9/1999 | Vollrath | |
| 6,036,635 A | 3/2000 | Altshuler | |
| 6,398,720 B1 | 6/2002 | Dabal | |
| 6,458,073 B1 | 10/2002 | Bonthuys | |
| 6,776,755 B1 | 8/2004 | Raskin | |
| 7,083,570 B2 | 8/2006 | Bonthuys | |
| 8,690,754 B2 * | 4/2014 | Smith ................ A61F 5/41 600/38 |
| 2004/0171911 A1 | 9/2004 | Zurita | |
| 2005/0033113 A1 | 2/2005 | Bonthuys | |
| 2008/0146870 A1 | 6/2008 | Marchello | |
| 2011/0270032 A1 | 11/2011 | Smith | |

* cited by examiner

*Primary Examiner* — John Lacyk
(74) *Attorney, Agent, or Firm* — Hoffman Warnick LLC

(57) ABSTRACT

A tractal erectile device is disclosed. In one embodiment, the device includes a hollow vessel having a first opening for receiving an organ, and a second opening for releasing fluid from within the vessel. The hollow vessel may include: an integral smooth lip portion surrounding the first opening for receiving an organ; an elongated cylindrical portion connected to the lip portion, an hour-glass portion connected to the elongated portion, and an ellipsoid shaped end portion including the second opening for releasing fluid from within the vessel.

18 Claims, 20 Drawing Sheets

Table 2 - Example Relative Partial Vacuum Via Deformation and Release

| Percent Side Wall Deflection of Radius, b | Percent of Original Radius, b | Internal Pressure (Initial = 15 PSI) | Internal Pressure Below Ambient (PSI) | SIZE 14, Organ Extraction Force (LBS) | SIZE 15, Organ Extraction Force (LBS) |
|---|---|---|---|---|---|
| 1% | 99.00% | 14.9 PSI | -.02 PSI | 0.04 | 0.05 |
| 5% | 95% | 14.3 PSI | -.70 PSI | 1.50 | 1.88 |
| 10% | 90% | 13.5 PSI | -1.5 PSI | 3.21 | 4.03 |
| 20% | 80% | 12.0 PSI | -3.0 PSI | 6.41 | 8.06 |
| 30% | 70% | 10.5 PSI | -4.5 PSI | 9.62 | 12.10 |
| 50% | 50% | 7.50 PSI | -7.5 PSI | 16.04 | 20.16 |
| 99% | 1% | 0.15 PSI | -14.85 PSI | 31.75 | 39.92 |

FIG. 20

TRACTAL ERECTILE DEVICE AND SEAL CAP

CROSS-REFERENCE TO RELATED APPLICATIONS

This application claims priority to U.S. provisional application Ser. No. 61/602,316, filed on Feb. 23, 2012, which is hereby incorporated by reference in its entirety.

FIELD

The subject matter disclosed herein relates to a tractal erectile device (e.g., an erectile aid). Specifically, the subject matter disclosed herein relates to solutions for stimulating a mammalian organ, such as a human organ. The subject matter further relates to a human organ stimulator and related methods.

BACKGROUND

Male Erectile Dysfunction (ED) is a condition that affects many men and can have a negative physical and psychological impact on their lives. Stimulation of the penis may be difficult for men suffering from ED, and although attempts have been made to treat ED, those attempts have failed to provide a safe and effective treatment.

BRIEF DESCRIPTION

A tractal device is disclosed. In one embodiment, the device includes a vessel having a first opening for receiving an organ (e.g., a penis), and a second opening for releasing fluid from within the vessel. The vessel may include: a lip portion forming the first opening for receiving the organ; an elongated portion connected to the lip portion, an hour-glass portion connected to the elongated portion, and an end portion including the second opening for releasing fluid from within the vessel. The erectile aid may include a one-way valve fluidly connected to the second opening, the one-way valve allowing for the release of fluid from within the vessel, while substantially preventing the entry of ambient air into the vessel. The erectile aid may further include a detachable seal cap having an arcuate or semi-circular slit for allowing the fluid to release from within the vessel to the ambient. The arcuate or semi-circular slit may be fluidly connected to bulbous, rounded or otherwise expanded openings extending along an axis of the seal cap. These bulbous, rounded, or otherwise expanded openings may increase the useable lifespan of the seal cap as it undergoes repeated movement due to the release of fluid from the vessel.

In another embodiment, the arcuate or semi-circular slit in the seal cap can be divided by one or more bridge element(s) or other support element(s). The bridge element(s) can divide the arcuate or semicircular slit into two or more sections. The bridge element can help to support the seal cap, and prevent bending or curling of the seal cap. Maintaining the structural integrity of the seal cap can help to provide an effective seal over the one-way valve, thereby enhancing the performance of the device.

In another embodiment, a device is disclosed, including: a vessel having a first opening for receiving an organ, and a second opening for releasing a fluid from within the vessel, the vessel including: a lip portion surrounding the first opening; an elongated portion connected to the lip portion; an hour-glass portion connected to the elongated portion; and an end portion including the second opening; and a one-way valve fluidly connected to the second opening, the one-way valve allowing for release of the fluid from within the vessel; and a seal cap connected to the one-way valve, the seal cap including a slit extending across an axial center of the seal cap.

In another embodiment, a device is disclosed, including: a vessel having a first opening for receiving an organ, and a second opening for releasing a fluid from within the vessel, the vessel including: a lip portion surrounding the first opening; an elongated portion connected to the lip portion; an hour-glass portion connected to the elongated portion; and an end portion including the second opening, wherein at least two of the elongated portion, the hour-glass portion and the end portion are connected via complementary semi-circumferential tabs extending respectively, from the at least two of the elongated portion, the hour-glass portion and the end portion.

BRIEF DESCRIPTION OF THE DRAWINGS

These and other features of this invention will be more readily understood from the following detailed description of the various aspects of the invention taken in conjunction with the accompanying drawings that depict various embodiments of the invention, in which:

FIG. 20 shows an example table illustrating relationships between deformation of an erectile aid and relative partial vacuum conditions within that erectile aid according to various embodiments.

It is noted that the drawings of the invention may not be to scale. The drawings are intended to depict only typical aspects of the invention, and therefore should not be considered as limiting the scope of the invention. In the drawings, like numbering represents like elements between the drawings.

DETAILED DESCRIPTION

Figure 1:
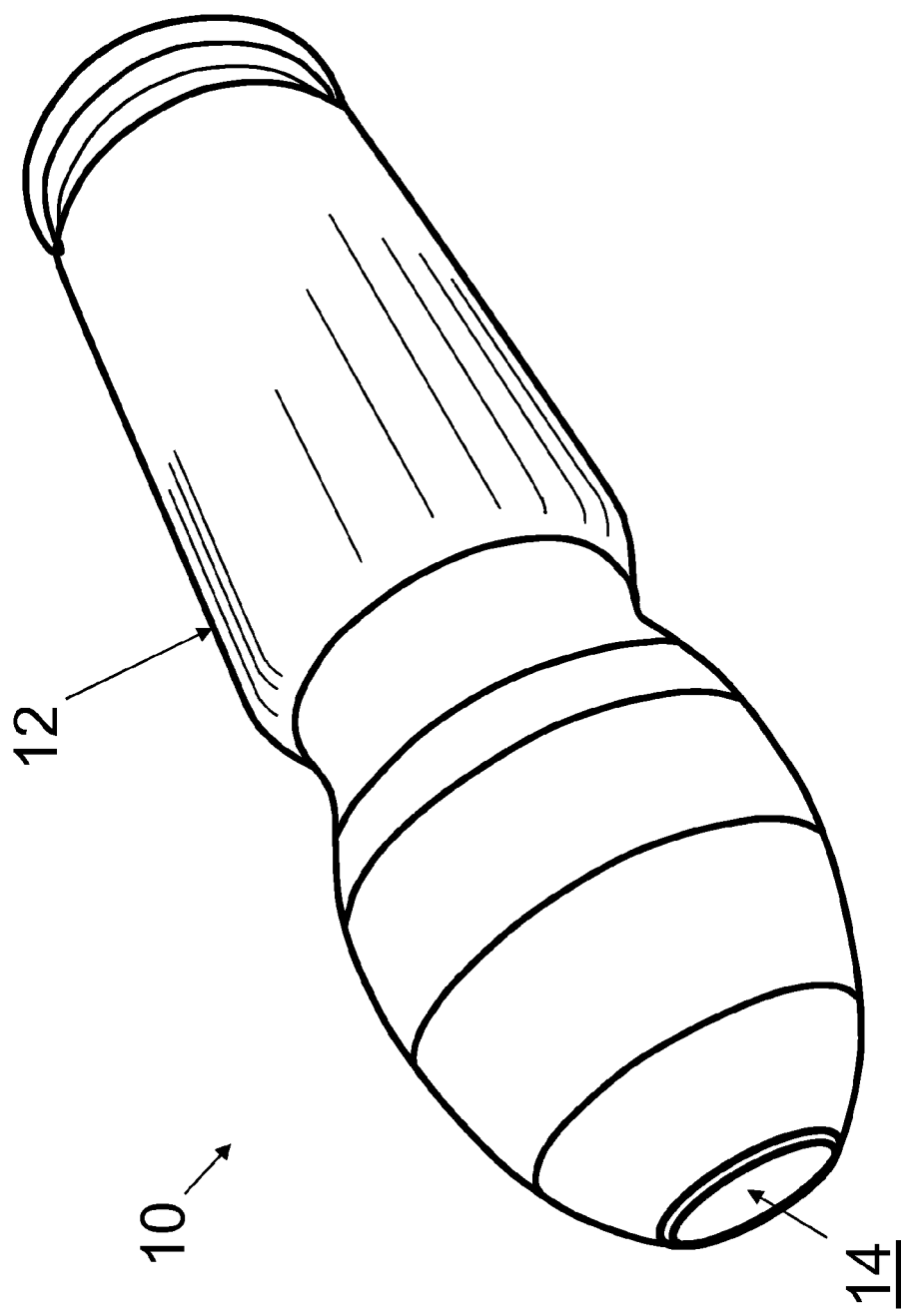
FIG. 1 shows a three-dimensional perspective view of a tractal erectile aid according to an embodiment.

Aspects of the invention provide for a tractal device (e.g., a tractal erectile aid, or TEA). As used herein, the term "tractal" may refer to the application of a tractile or tractive shearing force on an object. A "tractal" device may provide a tractile or shearing force by, e.g., pulling, pushing, or shaping an object using a motive shearing force (e.g., a back and forth motion). In one embodiment, the erectile aid includes a vessel having a first opening for receiving an organ (e.g., a penis), and a second opening for releasing fluid (e.g., air) from within the vessel. In one embodiment, the device (or, TEA) may be used to create a partial vacuum around an organ within the vessel, whereby the partial vacuum is created by the release of fluid from within the vessel. This fluid may be forced (in pulses) out of the vessel by sliding the vessel (e.g., with the aid of lubrication) to and fro axially along the shaft of the organ. Sliding the vessel along the axis of the organ may be actuated by, for example, a human operator. Motion along the axis of the organ inwardly toward the vessel's interior creates a momentary higher pressure zone within the vessel, whereby the organ creates a seal with the first opening, and whereby a seal cap (including, or connected to, a one-way valve) enables release of the slightly over-pressured entrapped fluid through the second opening. After the pressure differential between the inside of the vessel and the outside of the vessel overcomes the resistance of the valve and seal cap, fluid initially entrapped between the inner wall of the vessel and the organ is released, creating a suction effect on the organ, as the motion of the vessel is directed outwardly away from the vessel's interior along the axis of the organ. This pulsating reciprocal motion yields a net suction effect which may stimulate the organ and induce an erection. Reduced pressure inside the vessel walls may also act to increase the mutual tractive shear ("tractal") forces that are created across the lubricant boundary between the outer skin of the organ and the inner wall of the vessel. Reduced surrounding pressures and increased shear forces on the surface skin of the organ may enhance one's ability to obtain and sustain an erection.

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

As will further be understood from the description herein, portions of the device (or, TEA) may be formed of a substantially semi-flexible material (e.g., Shore A85 to Shore D50 hardness) that may "self-generate" a natural vacuum effect when interacting with an organ. That is, the inner surface of the device may provide a natural "pull" on the porous outer skin of the organ upon interaction with the device. In this sense, the interaction of the inner surface of the device with the skin of the organ may create a slight natural vacuum before the device is manipulated in one of the manners described herein. It is understood that the organ may provide a natural contractive force when engaged with the device, such that the vacuum effect may be initiated momentarily after placing the organ within the vessel portion of the device.

As will be described herein, when desirable, the seal cap, which acts as the top of the one-way valve, can be opened from a location external to the vessel, and the internal pressure may be released by pulling the seal cap upward. As is further described herein, the vessel's shape may aid in creating a suitable partial vacuum around the penis, thereby aiding in inducing and sustaining an erection.

Turning to FIG. 1, a three-dimensional perspective view of an erectile aid 10 is shown according to an embodiment. As shown, erectile aid 10 includes a vessel 12 and a seal cap 14. As described herein, seal cap 14 may allow for the release of fluid (e.g., air) from vessel 12 during operation of erectile aid 10, while also preventing ambient fluid flow from entering the vessel 12.

Figure 2:
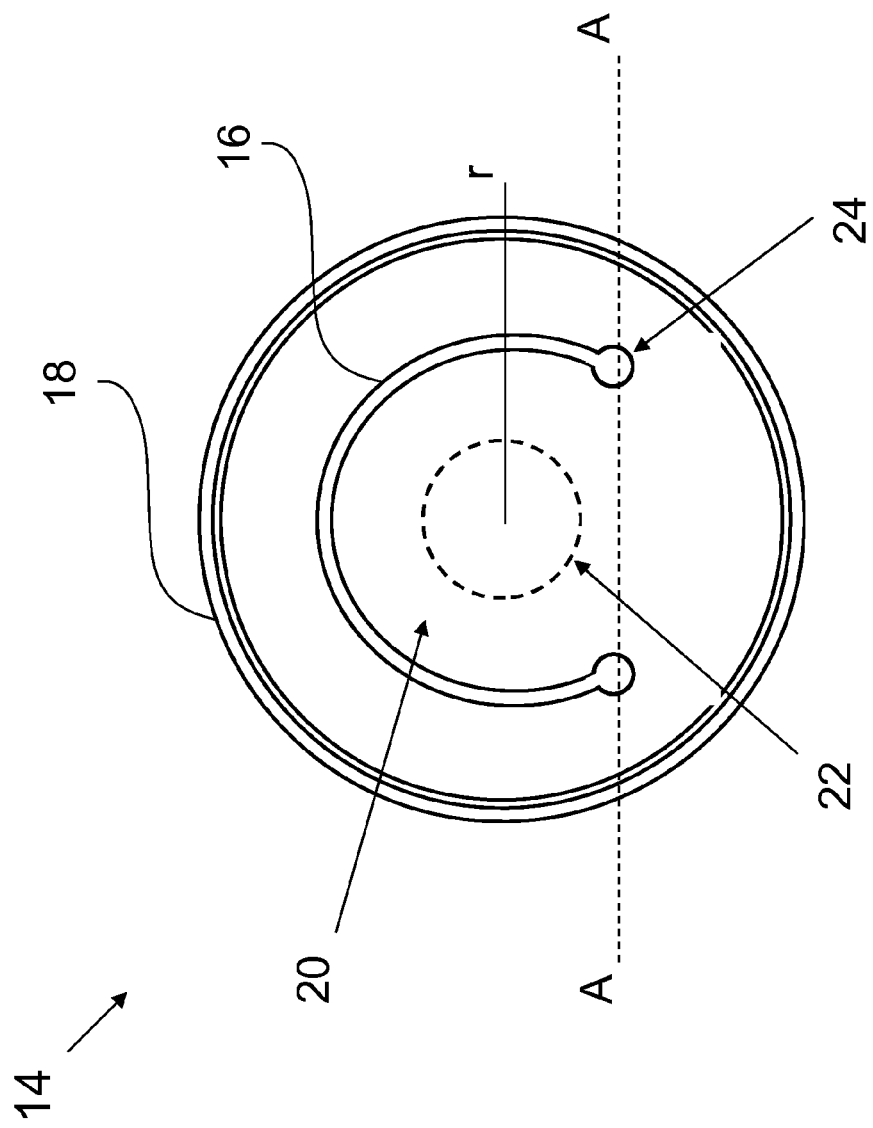
FIG. 2 shows an end view of an underside of a seal cap according to an embodiment.

Turning to FIG. 2, an end view of an underside of the seal cap 14 is shown according to an embodiment. As shown, seal cap 14 may include an arcuate or semi-circular slit or opening 16, which may allow for movement of a movably attached portion 20 of the seal cap 14. This movably attached portion 20 may be a pivotably attached flap or piece of seal cap 14. Slit 16 may be of a size sufficient to allow e.g., a human fingernail, to effectively enter the slit 16 and grip movably attached portion 20. Slit 16 may be tapered such that it provides a sufficient seal on the inner portion of the seal cap 14 (closer to interior of the vessel 10), while providing space to receive, e.g., a human fingernail on the outer portion of the seal cap 14. This tapering may further aid in creating an effective "flapper valve," restricting the flow of fluid in one direction while allowing flow in the opposite direction, as is described herein. The seal cap 14 may further include a lip or ring 18, which may allow seal cap 14 to be operably connected (sealed) to vessel 10.

Figure 6:
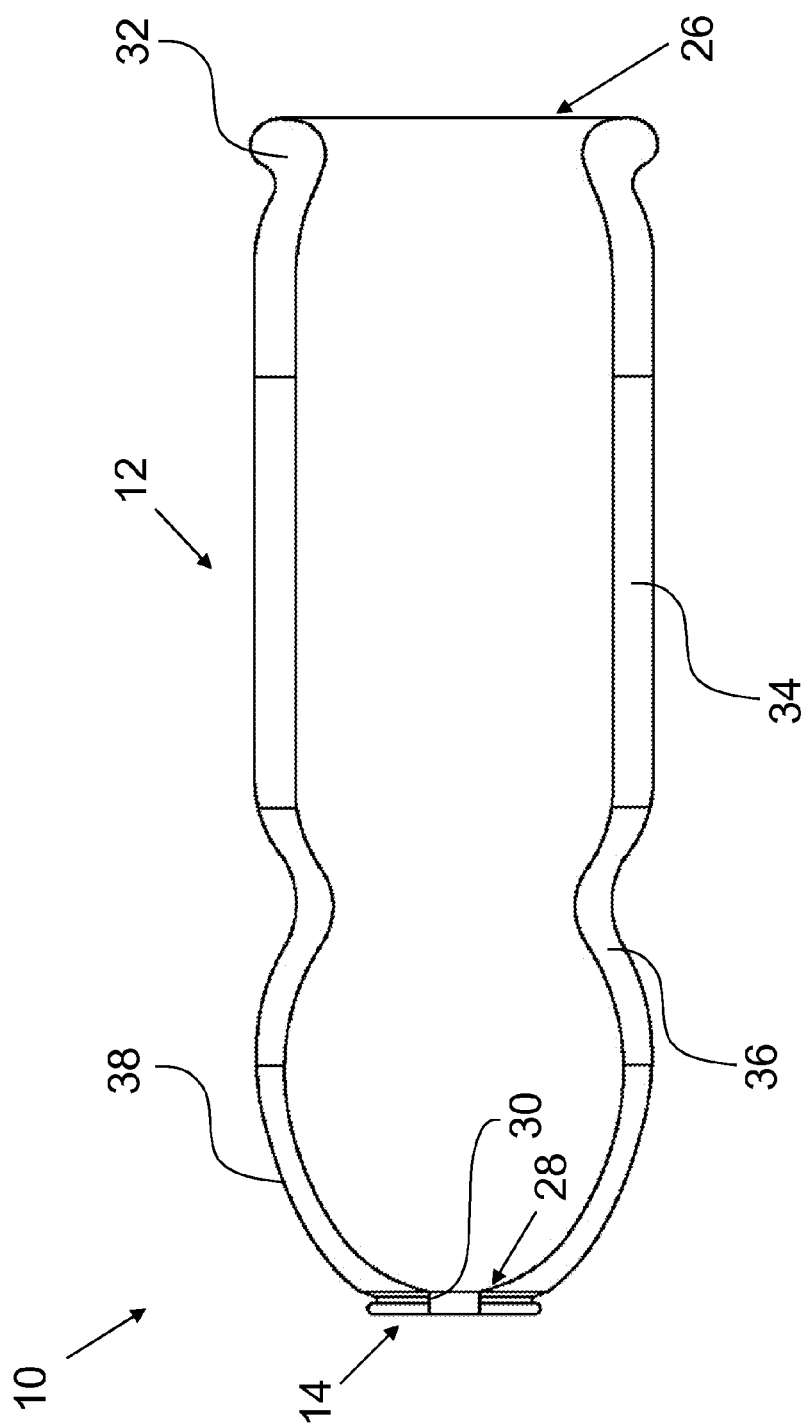
FIG. 6 shows a cross-sectional view of an erectile aid according to an embodiment.

In an embodiment, a portion 22 of the seal cap 14 may be configured to operably attach to a one-way valve 30 (See, FIG. 6). The one-way valve 30 may be any conventional one-way valve mechanism that allows a fluid (e.g., air) to flow in one direction, and restricts movement of fluid in the opposite direction. In one embodiment, the one-way valve 30 is attached to the portion 22 of seal cap 14 at approximately the center of the seal cap 14. However, in other embodiments, the one-way valve 30 can be configured to operably attach to another portion of the seal cap 14.

In any case, a portion 20 of the seal cap 14 may be configured to cover and mate intimately on its inner side with the outside surface of vessel 12 over and around the second opening 28 (FIG. 6) of vessel 12. The intimate mating of these two contactable surfaces may act as a one-way valve that allows a fluid to readily flow in an outward direction through opening 28, and to highly restrict movement of fluid in the opposite direction, i.e., inwardly around portion 20 and through the second opening 28 of vessel 12. In one embodiment, the outwardly directing one-way valve 30 is located approximately at the center of the seal cap 14. However, in other embodiments, the one-way valve 30 may be configured to operably attach to another non-concentric portion of seal cap 14 (e.g., on one or more sidewalls, corresponding to one or more openings). Additional openings and one-way valves (e.g., similar to seal cap 14) may be used in other embodiments.

Further shown in FIG. 2 are openings 24 fluidly connected to slit 16. Openings 24 may be bulbous, rounded, or otherwise expanded (e.g., squared, diamond-shaped, etc.) extensions of the slit 16, and may form an axis (A-A, shown in phantom) about which slit 16 may be pivotably actuated (e.g., pulled by a human fingernail). As shown, axis A-A may be off-set from a central axis (shown as radius r), however, it is understood that axis A-A may be aligned with the central axis in one embodiment. Openings 24 may allow for repeated opening and closing of the movably attached portion 20 (or, flap) while minimizing material fatigue. That is, openings 24 may allow seal cap 14 to remain operable as designed for a greater number of cycles by reducing the material fatigue on seal cap 14, specifically along axis A-A.

Figure 3:
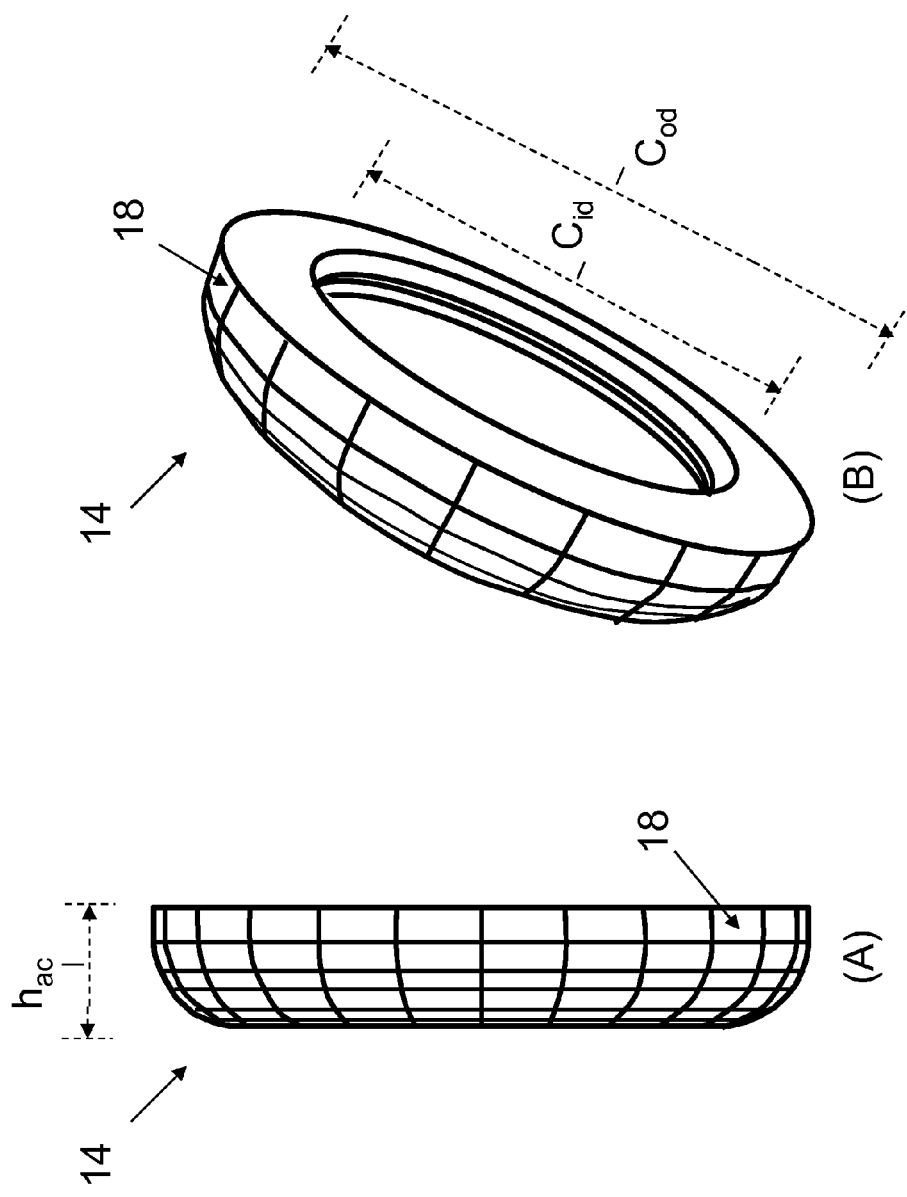
FIG. 3A shows a three-dimensional side view of a seal cap according to an embodiment.
FIG. 3B shows a three-dimensional perspective view of a seal cap excluding a slit according to an embodiment.

Turning to FIGS. 3A-3B, side and three-dimensional perspective views of the seal cap 14 excluding the one-way valve are shown, respectively. In one embodiment, seal cap 14 may have an inner cup diameter ($C_{id}$) of approximately 0.85 inches (0.60 to 1.00 inch range of diameters) and may have an overall axial cup height ($h_{ac}$) of approximately 0.180 inches (0.100 to 0.200 inch range of total heights). In one embodiment, seal cap 14 may have an overall outer cup diameter ($C_{od}$) of approximately 1.00 inches (0.75 to 1.20 inch range of outer diameters). In one embodiment, the outer periphery of the seal cap lip may have a cross axis radius of curvature of approximately 0.150 inches (0.125 to 0.180 inch range of radii curvatures).

Figure 4:
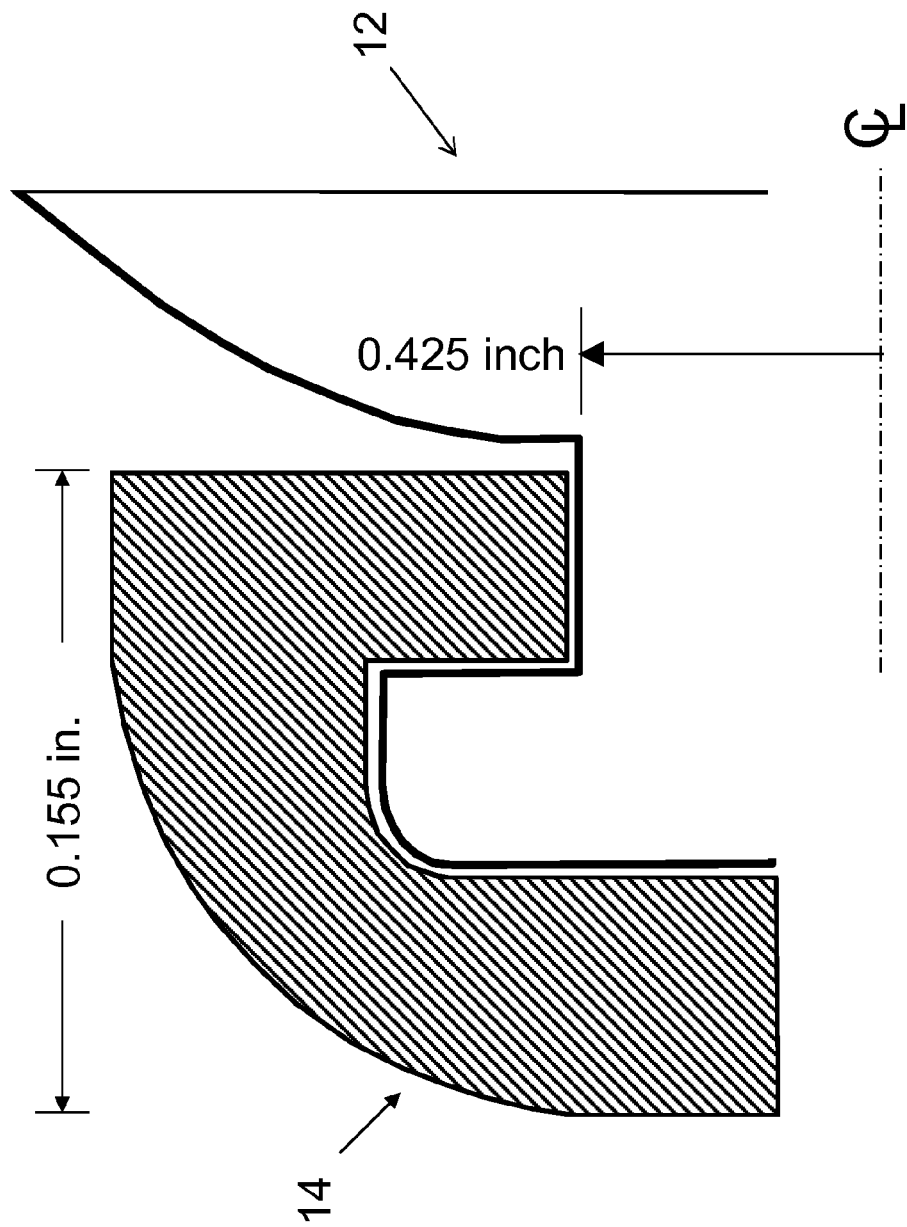
FIG. 4 shows a schematic view of dimensional relationships between portions of a seal cap and a vessel's end portion according to an embodiment.

Turning to FIG. 4, a schematic view of dimensional relationships between portions of the seal cap 14 are shown according to an embodiment. In one embodiment, the portion 22 (FIG. 2) of seal cap 14 configured to operably connect to the one-way valve may have a curvature radius which is off-set from the axis of symmetry of the seal cap 14 but in a plane which includes the symmetry axis of approximately 0.155 inches (0.120 to 0.175 inches range of curvature radii).

Figure 5:
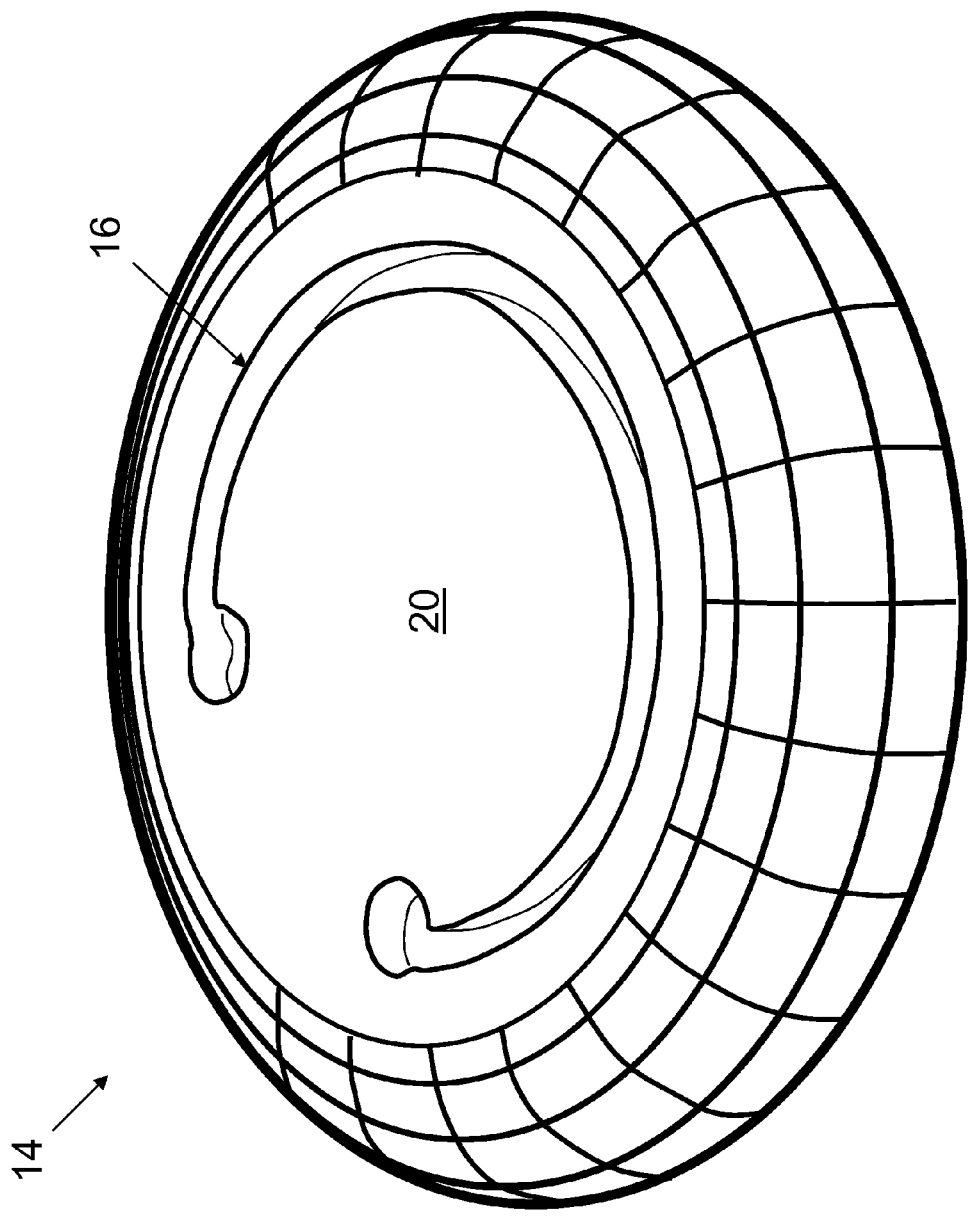
FIG. 5 shows a three-dimensional perspective view of a top portion of a seal cap according to an embodiment.

FIG. 5 shows a three-dimensional perspective view of a top portion of the seal cap 14 according to an embodiment. In one embodiment, slit 16 may be 0.040 inches wide (0.020 to 0.060 inches range of widths), substantially large enough, e.g., to receive a human fingernail which may pull the movably attached portion 20 upward and away from the vessel 12 (not shown) to release pressure (e.g., in excess of ambient) which may be held within the vessel 12.

FIG. 6 shows a cross-sectional view of an erectile aid 10 according to an embodiment. As shown, erectile aid 10 may include the vessel 12 and the seal cap 14. Vessel 12 may include a first opening 26 for receiving an organ, and a second opening 28 for releasing fluid (e.g., air) from within the vessel 12. Also shown in FIG. 6 is a one-way valve 30, which may be any conventional one-way valve allowing for the flow of a fluid in one direction. One-way valve 30 may be configured to sealingly fit within the second opening 28. That is, one-way valve 30 may be configured to substantially completely fill the second opening 28 (e.g., using an expandable ring or other sealing mechanism. In this embodiment, fluid exiting from the second opening 28 is directed through one-way valve 30. However, in another embodiment described herein, seal cap 14 may act as a valve mechanism and one-way valve 30 may not be used.

Erectile aid 10 may also include a lip portion 32, which may form a tapered ring surrounding first opening 26. Lip portion 32 may form a ring having a diameter sufficient to allow a penis to enter first opening 26. Erectile aid 10 may further include an elongated portion 34 connected to the lip portion 32. Elongated portion 34 may have a length ranging from approximately 1.0 inch to approximately 6.0 inches. Further shown in FIG. 6 is an hour-glass portion 36, which is substantially tapered toward a point internal to a wall of the elongated portion 34. That is, the hour-glass portion 36 bows or curves inward from the inner wall of elongated portion 34 (and does so similarly from the end portion 38). This hour-glass portion 36 may aid in forming a substantial seal and increase the tractive forces between a portion of an organ within the vessel 12 and a portion of an internal wall of vessel 12. Parts of the end portion 38 may have a substantially similar inner and outer diameter as portions of the elongated portion 34.

In two illustrative examples listed below in Table 1, two overall erectile aid 10 (also known as "device") sizes and corresponding dimensional relationships are provided:

TABLE 1

|  | Device Sizes (Inches) | |
| --- | --- | --- |
|  | Small | Large |
| Length | 7.00 | 7.50 |
| Shell Thickness | 0.140 | 0.140 |
| Top Dome Concentric Hole Dia. | 0.250 | 0.250 |
| Top Dome Max O.D. | 2.140 | 2.340 |
| Top Dome Min. I.D. | 1.860 | 2.060 |
| Dome Length | 1.500 | 1.500 |
| Hour Glass Restriction Max. O.D. | 1.860 | 2.020 |
| Hour Glass Restriction Min. I.D. | 1.580 | 1.740 |
| Hour Glass Length | 1.500 | 1.500 |
| Cylinder Max. O.D. | 2.140 | 2.340 |
| Cylinder Min. I.D. | 1.860 | 2.060 |
| Cylinder Length | 2.500 | 3.000 |
| Opening End Max. O.D. | 2.140 | 2.340 |
| Opening End Restriction Max. O.D. | 2.200 | 2.200 |
| Opening End Min. I.D. | 1.600 | 1.760 |
| Opening Length | 1.500 | 1.500 |

In Table 1, "shell" may be the wall thickness of the material forming erectile aid 10, the "top dome" may represent the end portion 38, "cylinder" may represent the elongated portion 34, and the "opening end" may represent the portion of erectile aid 10 formed by lip 32 and its adjacent tapered portion.

It is understood that as shown and described herein, the seal cap 14 may be continuously connected with the body of the vessel 12 in some embodiments. That is, the seal cap 14 may be molded or otherwise formed along with the vessel 12 to form a substantially continuous structure.

Figure 7:
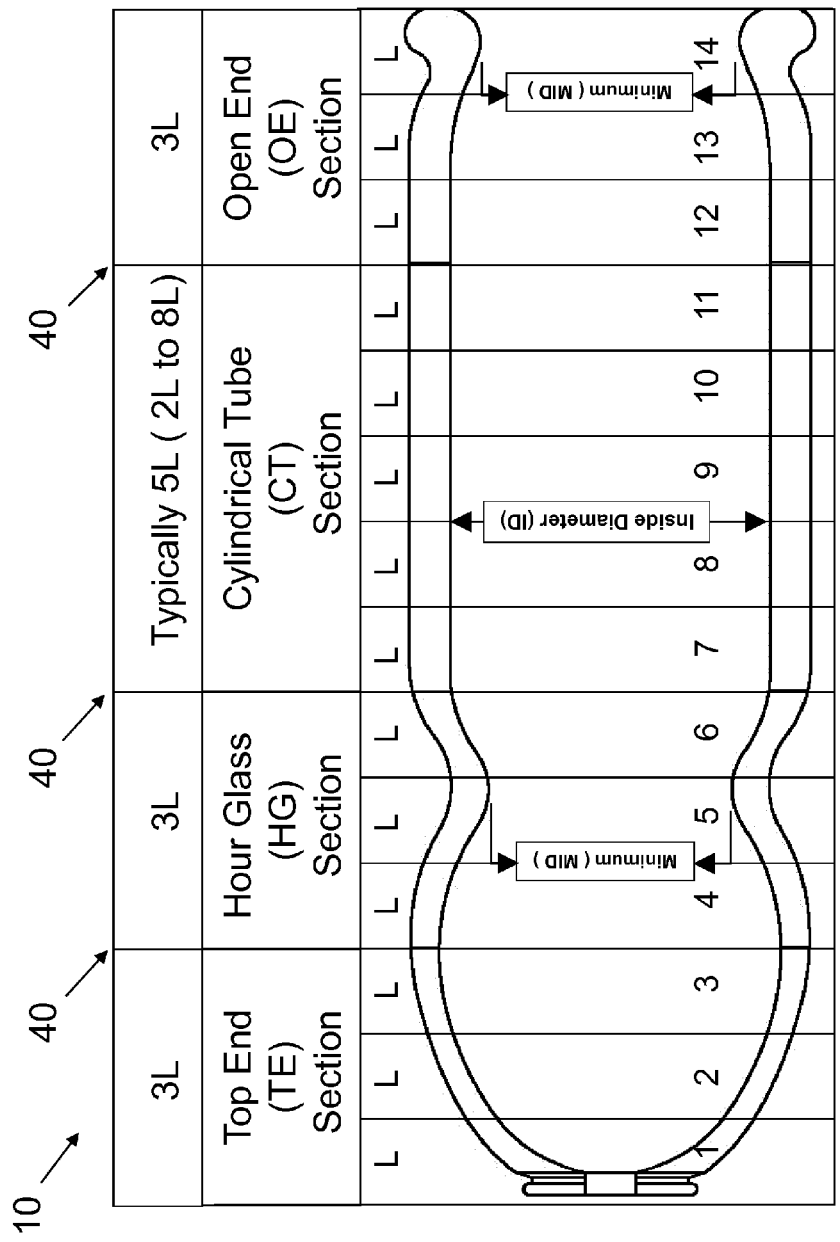
FIG. 7 shows a cross-sectional view of the erectile aid of FIG. 6, further including dimensional relationships according to an embodiment.

FIG. 7 provides a further illustrative cross-sectional view of the erectile aid 10 of FIG. 6, further including dimensional relationships according to an embodiment. For example, in FIG. 7, it is shown that the overall length of erectile aid 10 may be approximately 11-17 units of length ("L"), and that the erectile aid 10 may be partitioned to include at least three joints 40 between its sections (e.g., between Section TE and Section HG, between Section HG and Section CT, and between Section CT and Section OE, explained further herein). These joints 40 may allow erectile aid 10 to be disassembled and assembled by interlocking parts. These joints 40 may be formed with or without any adhesive (e.g., a tape or paste) or threaded mechanisms (e.g., male and female threads). Further, these joints 40 may be formed by corresponding male and female flanges arranged such that components of the erectile aid may be pulled apart or pushed back together with minimal human effort. Further, it is understood that joints 40 will be flush with the internal walls of erectile aid 10, such that when assembled, erectile aid 10 provides a substantially smooth internal surface to receive an organ (e.g., a penis). In one embodiment, joints 40 are also flush with the external walls of erectile aid 10, such that when assembled, erectile aid 10 provides a substantially smooth external surface. In one embodiment, the erectile aid 10 may be divided into four parts (having three joints 40) and may be arranged in, e.g., a kit or carrying case. The disassembled erectile aid 10 may resemble a substantially unidentifiable array of components when disassembled and placed in e.g., a kit or carrying case.

Figure 8:
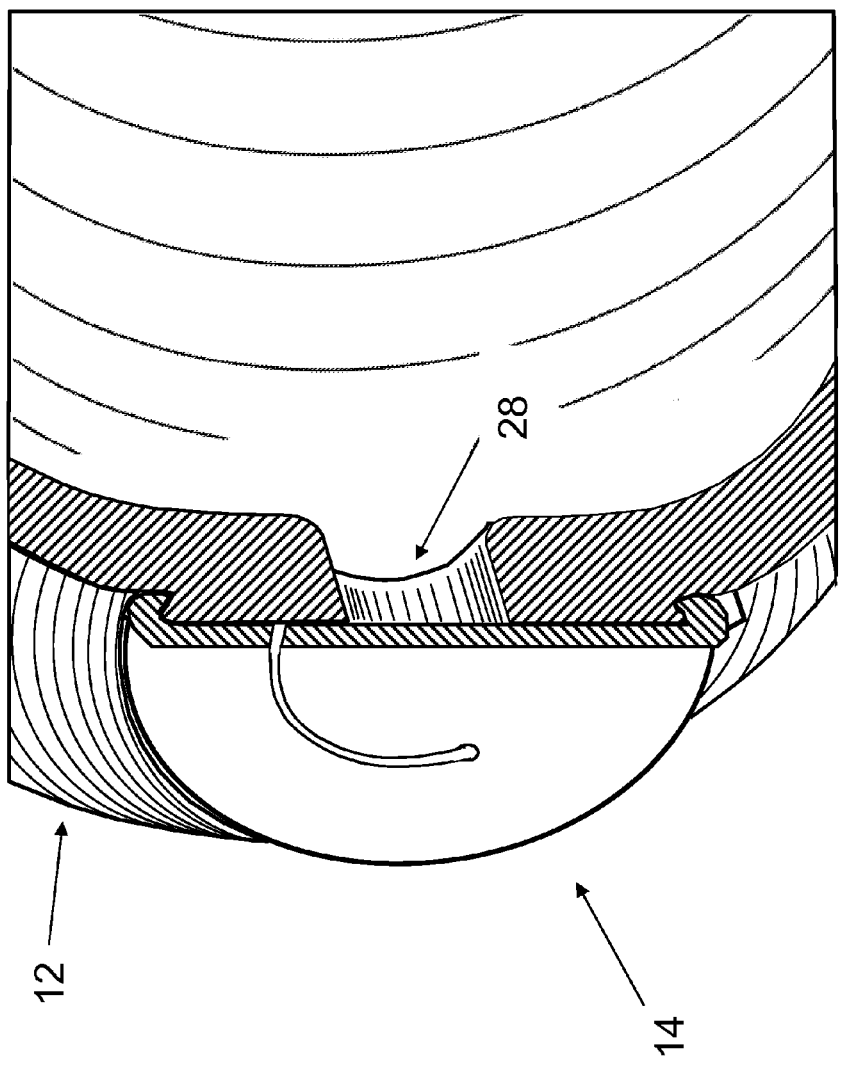
FIG. 8 shows a partial cut-away three-dimensional view of an erectile aid according to an embodiment.

FIG. 8 shows a partial cut-away of a three-dimensional view of an erectile aid according to an embodiment. As shown, in one embodiment, seal cap 14 may fit substantially flush with the axial outer portion of opening 28 such that seal cap 14 and opening 28 may function as an effective one-way valve. That is, as pressure increases within the vessel 12, fluid (e.g., air) within the vessel 12 is allowed to exit the opening 28, while the weight, shape and structure of the seal cap 14 prevents ambient fluid from entering the inner chamber of the vessel 12.

Figure 9:
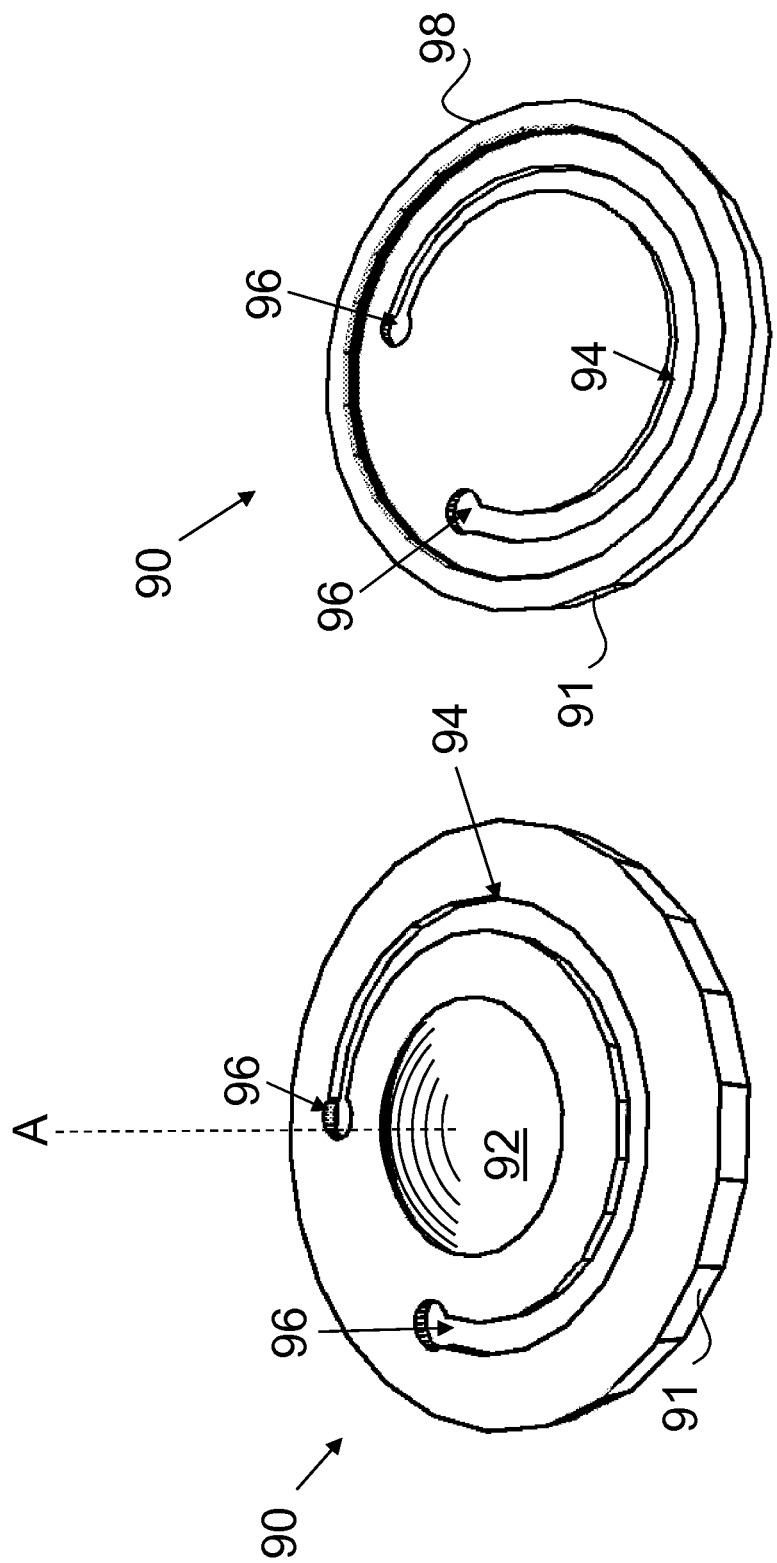
FIGS. 9A and 9B show three-dimensional perspective top and bottom views, respectively of a seal cap according to embodiments.

FIGS. 9A and 9B show three-dimensional perspective top (9A), and bottom (9B) views of a seal cap 90 according to embodiments of the invention. The seal cap 90 may be substantially rounded (or segmented-rounded) at its radial edges 91, whereby the seal cap 90 appears substantially circular from a top-down perspective. In an embodiment, the radial edges 91 may include notches, grooves or segments (segments shown) which may allow for improved grip of the seal cap 90. As described herein, the seal cap 90 may include an arcuate or semi-circular slit 94 for allowing the fluid to release from within the vessel to the ambient. The slit 94 may include at least one bulbous line end 96, which may help to alleviate the material fatigue placed on portions of the seal cap 90 proximate the axis about which the seal cap 90 pivots. In some embodiments, the arcuate or semi-circular slit 94 may extend between approximately 270 degrees and approximately 330 degrees along a circle having a central axis (A) being coaxial with a primary axis of the elongated portion (FIG. 7). That is, the semi-circular slit 94 may extend nearly completely around an inner circumference of the seal cap 90, such that the bulbous line ends 96 are separated from one another by approximately 30 to 90 degrees.

Also shown in FIG. 9A is a reinforcing member 92 affixed to a surface of the seal cap 90 between a center point (denoted by the origin of axis A) of the seal cap 90 and a portion of the slit 94. That is, the reinforcing member 92 may be used to reinforce the portion of the seal cap 90 configured to rotate away from the vessel 12 and release pressure from within the vessel 12. The reinforcing member 92 may include a protrusion (e.g., a bulbous or rounded protrusion as shown) configured to provide mechanical strength and weight to the seal cap 90. The reinforcing member 92 may help to ensure that positive pressure generated within the vessel is contained during operation, and may help to relieve mechanical stress on the portion of the seal cap 90 located between the slit 94 and the cap center point (denoted by the origin of axis A). In some cases, the reinforcing member 92 may be integrally formed with the surface of the seal cap 92 (e.g., via fabrication such as molding). In other cases, the reinforcing member 92 may be affixed to the surface of the seal cap 90 as an additional component (e.g., via an adhesive such as a glue).

Figure 10:
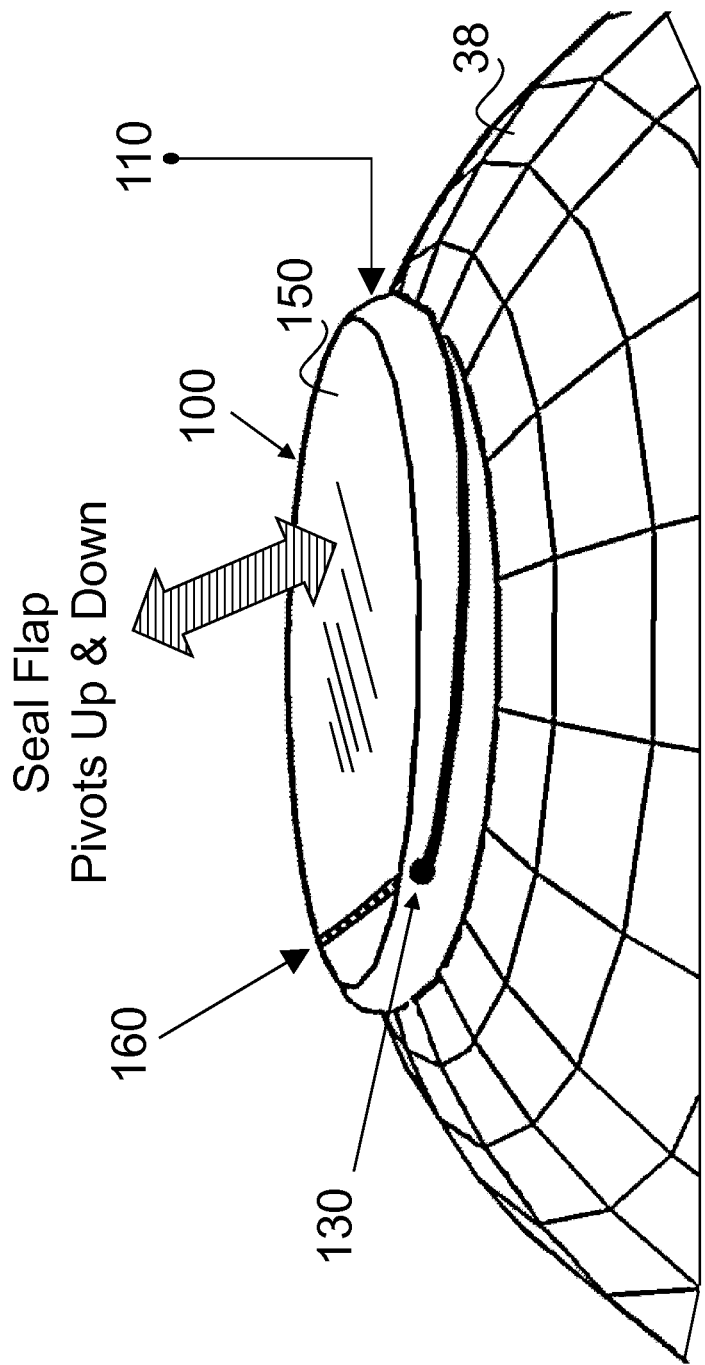
FIG. 10 shows a three-dimensional isometric view of an embodiment of a seal cap.

Turning to FIG. 10, a three-dimensional isometric view of another embodiment of a seal cap 100, shown in conjunction with the end portion 38, is illustrated. This embodiment includes one example of an integral continuous seal, as described herein. In this case, the seal cap 100 may include substantially rounded (or segmented) outer (radially outer) edges 110, and a slit 120 extending from a first location along the substantially rounded outer edge 110 to a second location (not visible in this perspective) along the substantially rounded outer edge 110. Similar to other embodiments described herein, the slit 120 may include at least one bulbous line end 130, which may aid in reducing the mechanical fatigue on the seal cap 100, in particular, in areas proximate the bulbous line end 130. In one embodiment (shown), the bulbous line ends 130 are located proximate the top surface 140 of the seal cap 100. As is also shown, the slit 120 may extend axially away from the bulbous line ends 130, such that a distance between the top surface 140 of the seal cap 100 and the bulbous line ends 130 is less than a distance between the top surface 140 and other portions of the slit 120 (in particular, those portions of the slit farthest from the bulbous line ends 130). In other terms, the slit 120 may extend from each bulbous line end 130 axially downward (toward the end portion 38), defining a tapered flap 150, which has a greater volume of material at its outer circumference than at portion proximate the bulbous line ends 130. This tapered flap 150 may pivot about an axis (or, pivot line) 160 along the seal cap 100. In some embodiments, this pivot line 160 may be reinforced with a resilient material such as a self-curing silicone rubber sealant, or other adhesive filler, to aid in reducing material fatigue. It is understood, however, that the pivot line 160 may not necessarily be reinforced in all embodiments. Therefore, the tapered flap 150 may be more heavily weighted at locations farther from the pivot line 160, providing a greater downward force at locations along the substantially rounded outer edge 110 than at locations closer to the center of the cap. This may help to counteract the positive pressure forces that may accumulate within the end portion 38 (and the vessel 12 as a whole) during operation.

Figure 11:
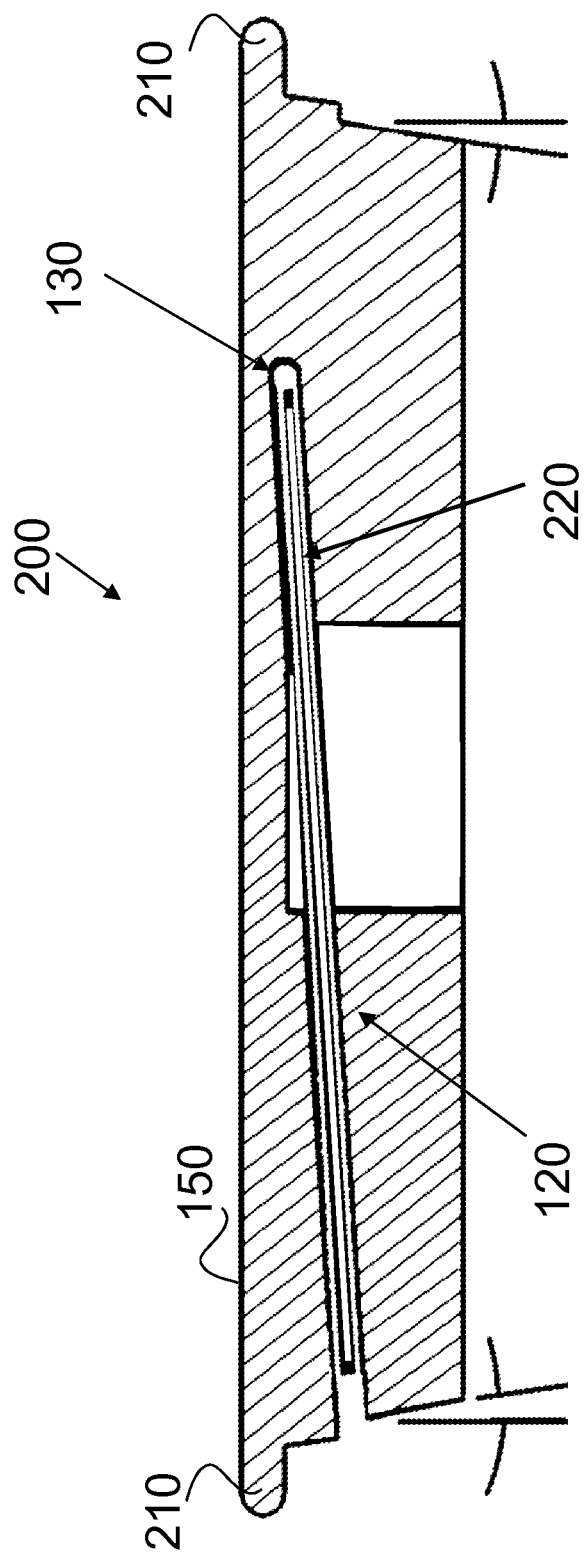
FIGS. 11-12 show cut-away side views of cap configurations according to embodiments.
Figure 12:
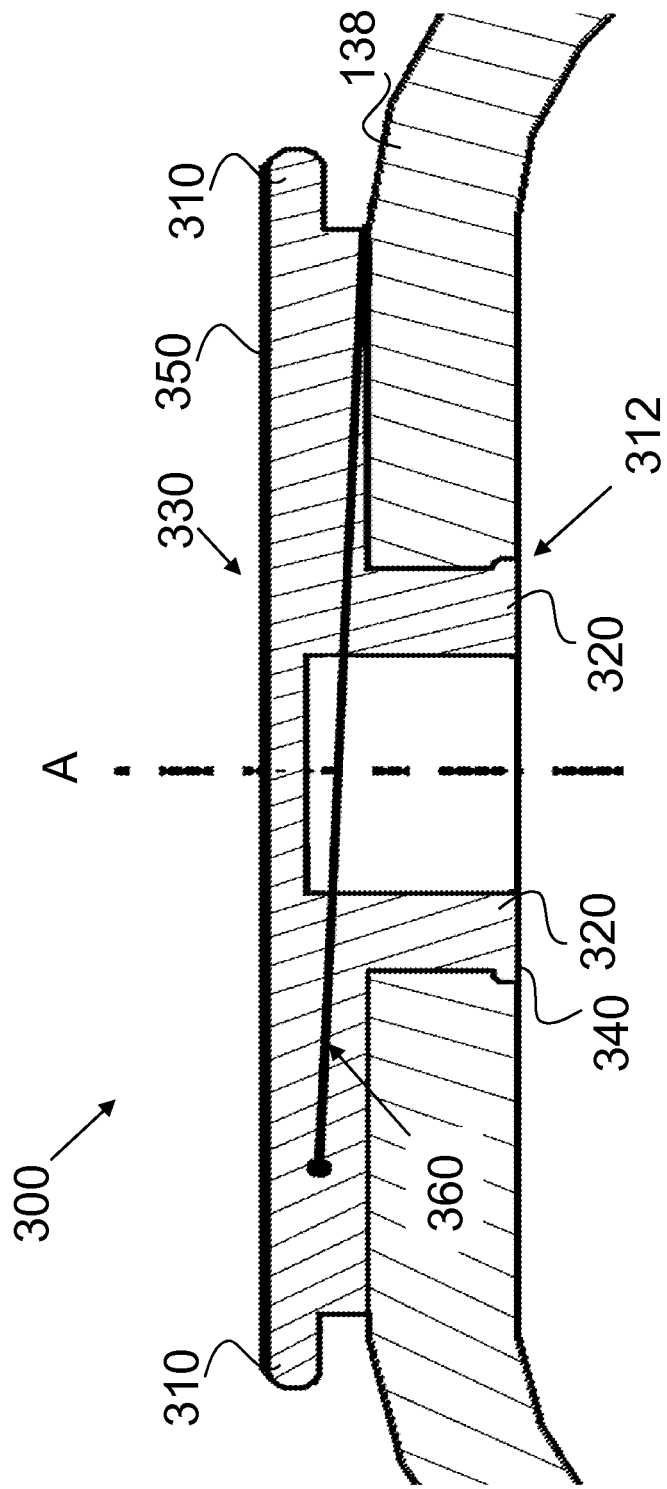

FIGS. 11-12 show cut-away side views of additional cap configurations according to embodiments of the invention. Turning to FIG. 11, a cap 200 is shown, which may include similar features as noted with respect to the cap 100 of FIG. 10. However, cap 200 includes a rim 210 along its outer circumference, which may aid in gripping the tapered flap 150 for the purposes of releasing pressure from within the vessel. Further, the rim 210 may provide additional weight to the tapered flap 150, which may counteract the positive pressure forces that may accumulate with the vessel during operation.

FIG. 12 shows a partial cut-away view of a cap 300, and part of an end portion 138 according to embodiments of the invention. As shown, the end portion 138 may include an opening 310 configured to receive partially complementary portions 320 of the cap 300. The partially complementary portions 320, which in actuality may be an annular extension from the top portion 330 of the cap 300, can include a lip, ridge or other protrusion 340 configured to engage a surface of the end portion 138, allowing the cap 300 to remain in place within the end portion 138 even while movement of the flap 350 is actuated (e.g., via rim 310, similar to the rim 210 of FIG. 11). In this case, the slit 360 in cap 300 may extend to a surface of the end portion 138, such that a portion of the flap 350 contacts a surface of the end portion.

Figure 13:
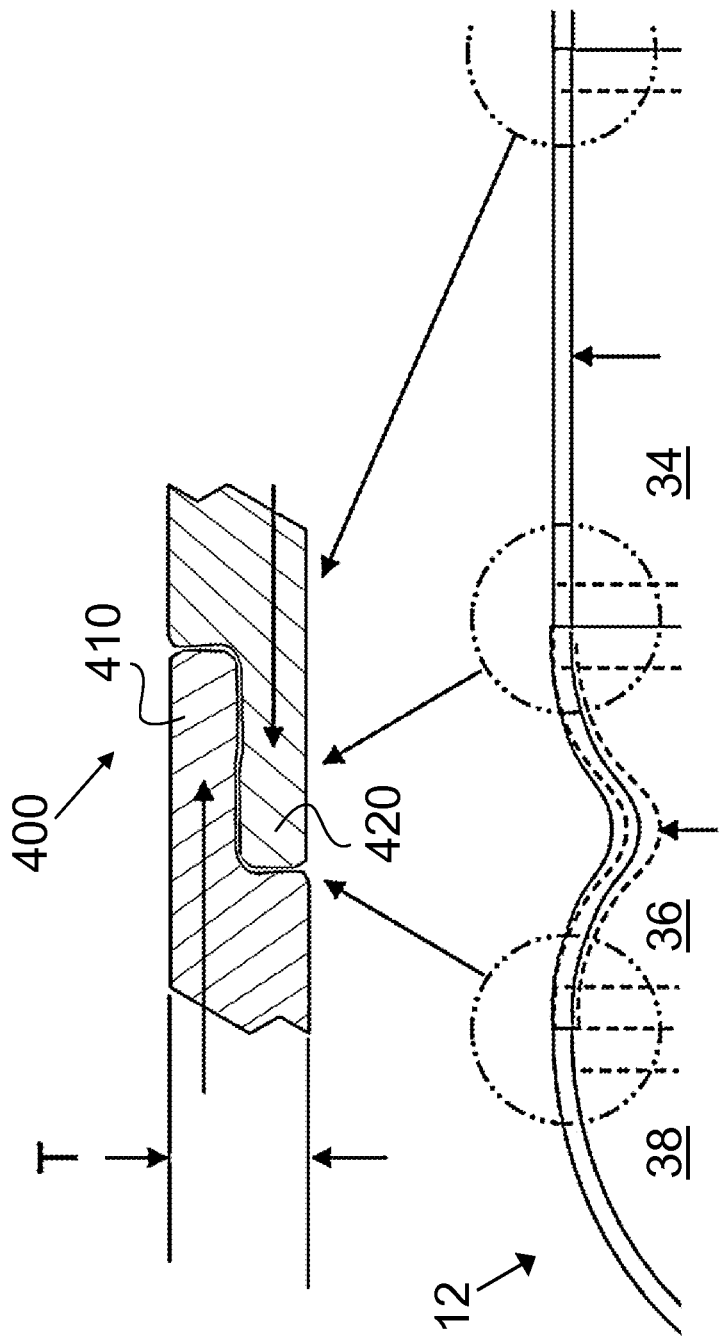
FIG. 13 shows a partial blow-up view of a joint between portions of a vessel according to embodiments.

FIG. 13 shows a partial blow-up view of a joint 400 between portions (e.g., end portion 38 and hourglass portion 36, and/or hourglass portion 36 and elongated portion 34, etc.) of the vessel 12 described herein. The joint(s) 400 may be formed in a variety of manners, a non-exhaustive listing of which is described herein. In any case, it is understood that the vessel 12 may be formed of a plurality of segments (or, portions), configured to be relatively easily connected and disconnected, e.g., by a human operator. The ability to connect and disconnect portions of the vessel 12 may allow for several benefits over conventional erectile aid devices. For example, the ability to connect and disconnect portions of the vessel 12 may allow for conservation of space during transport, storage or other non-functioning activities. Additionally, the ability to disconnect portions of the vessel 12 may enable discreet transportation and/or storage, allowing the possessor of the vessel 12 to avoid potentially unwanted inquiries regarding the erectile aid 10.

FIG. 13 illustrates one "snap-lock" approach to joining adjacent portions of the vessel 12, whereby each adjacent portion includes a semi-circumferential tab 410, 420, where the pair of semi-circumferential tabs 410 are complementary. In one case, the semi-circumferential tab may face radially outward (420), creating a recess located radially outward of the tab. In another case, the semi-circumferential tab may face radially inward (410), creating a recess located radially inward of the tab. In another embodiment, the semi-circumferential tabs 410, 420 may be magnetically joined together via opposing magnets (included in complementary tabs). In another embodiment, semi-circumferential tabs 410, 420 may be forced together via the vacuum forces within the vessel 12 during operation. That is, the semi-circumferential tabs 410, 420 may provide a complementary fit such that they remain in place prior to interaction with the organ, however, after interaction with the organ, the force between semi-circumferential tabs 410, 420 may be increased due to the vacuum effect within the vessel 12.

Figure 14:
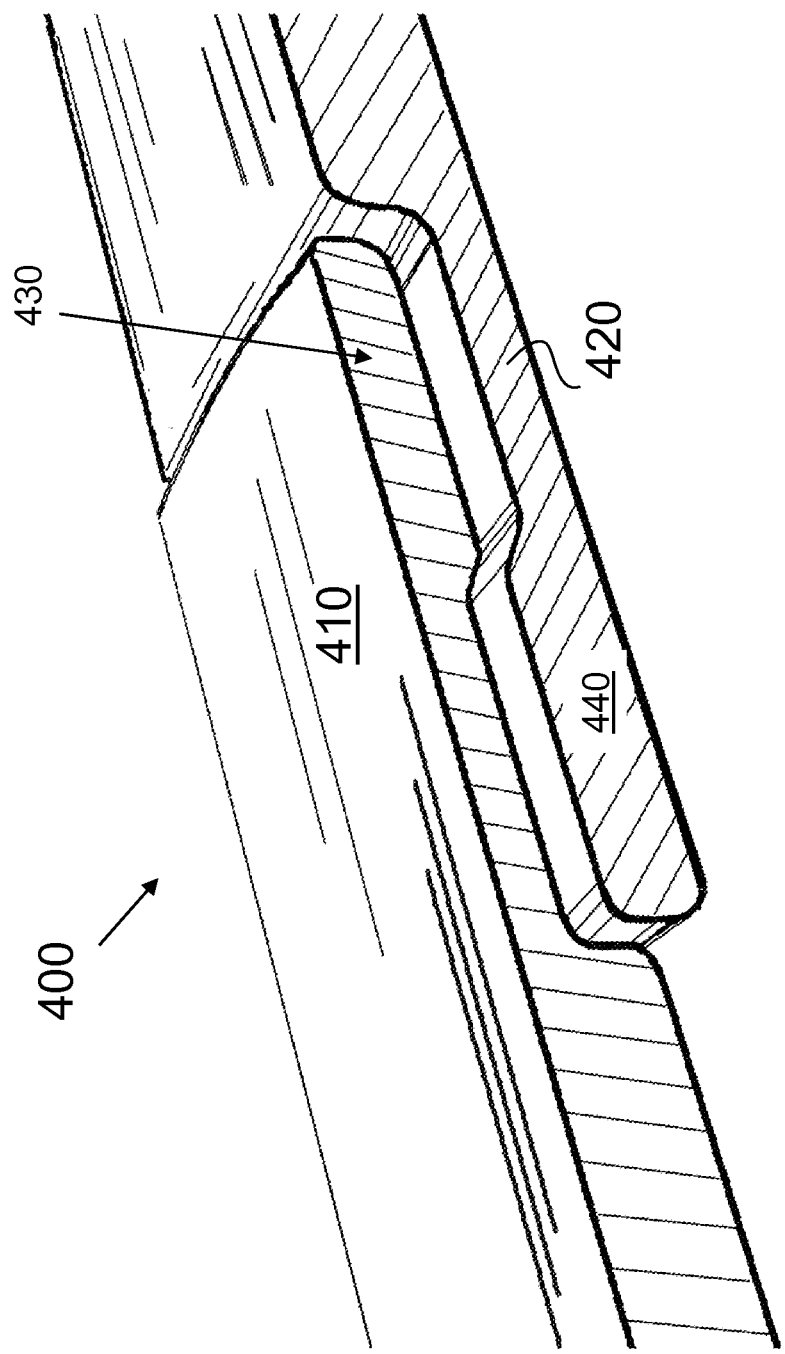
FIG. 14 shows a close-up three dimensional perspective view of the joint of FIG. 13.

FIG. 14 shows a close-up three dimensional perspective view of the joint 400 of FIG. 13. As shown, each semi-circumferential tab 410, 420 may include a radially extending portion 430, 440, respectively. In this case, the radially extending portions 430, 440 may engage one another to prevent axial sliding of the portions of the vessel 12. It is understood that the joint 400 shown only includes a portion of each semi-circumferential tab 410, 420. In some cases, the semi-circumferential tabs (e.g., 410, 420) may extend around an entire annulus of the vessel 12. In some other cases, however, the semi-circumferential tabs may extend around part of (e.g., half of) the annulus of vessel 12. In some cases, the semi-circumferential tabs may form bayonet-like joints.

Figure 15:
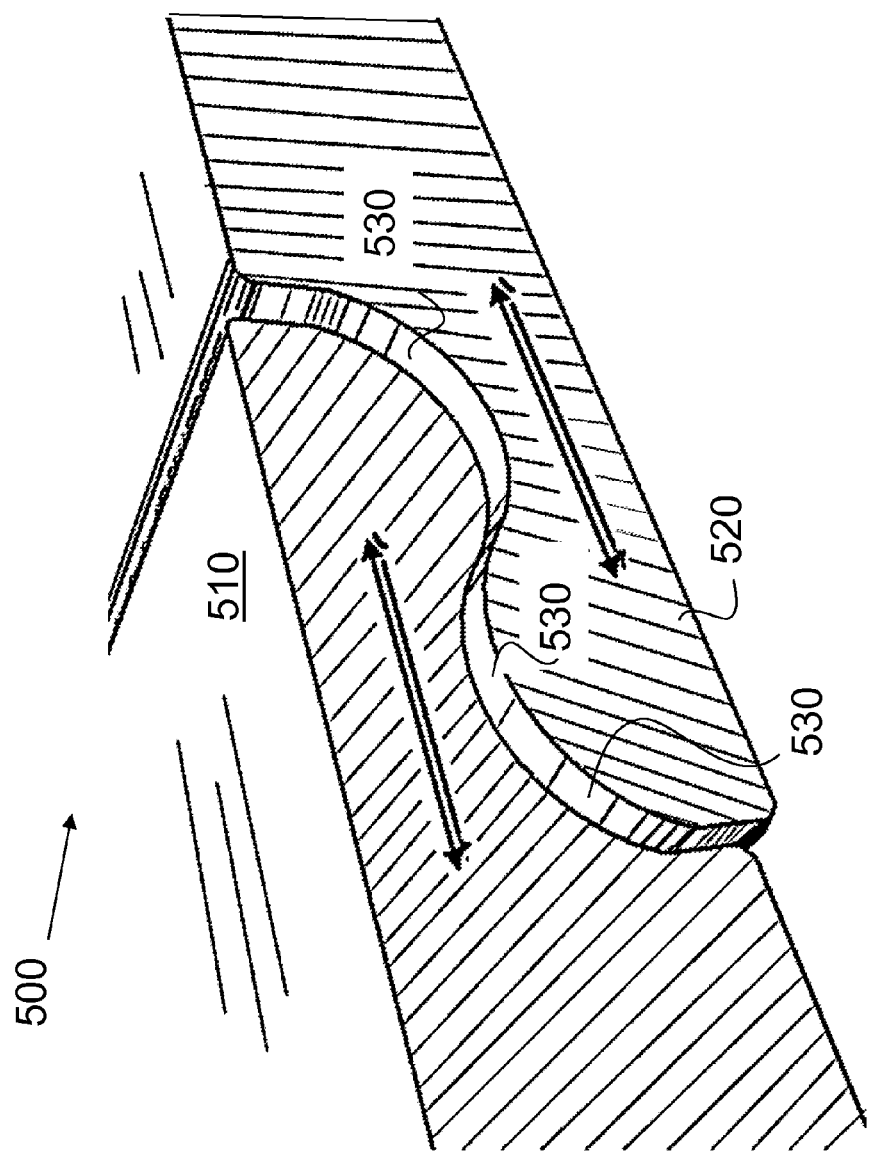
FIG. 15 shows a joint between portions of a vessel according to embodiments.

FIG. 15 shows an alternative embodiment of a joint 500 formed by complementary semi-circumferential tabs 510, 520. In this embodiment, each semi-circumferential tab 510, 520 may include a multi-segmented surface composed of segments 530. Adjacent segments 530 may be angled with respect to one another such that they form "S-shaped" ledges and corresponding recesses. These ledge/recess combinations may be used to lock the semi-circumferential tabs 510, 520 together, thereby engaging adjacent portions of the vessel 12.

Materials Examples:

Suitable materials for forming erectile aid 10 may include, e.g., United States Food and Drug Administration (FDA) approved plastics typically used in medical applications, such as VERSAFLEX™ HC TPE plastic or other similar materials having extremely low extractables and being free from phthalates or halagens. The hardness of the plastic may be approximately 85-95 (or harder) on the "Shore A" durometer scale. Further, a polished finish can be applied to the plastic, whereby the interior and/or exterior surfaces of the erectile aid 10 may have a surface finish roughness of approximately less than 10-30 micro-inches. The exterior may optionally be frosted and/or over molded over some portions for tactile ("tractal") purposes.

Characteristics of an example tractal erectile aid 10 are described below, in a merely illustrative example:

Parts:

The main product (e.g., erectile aid 10, FIGS. 6-7) may be constructed of one single plastic molded unit. Seal caps 14 can be approximately 0.5 inches to approximately 2 inches in diameter. The design of each part can be axially symmetric and the main body (e.g., vessel 12) can be tubular in nature. Two restrictive diameters can be designed within the main body (e.g., vessel 12). One is to be an approximate radial restriction of 0.15 inches in the hour-glass shape portion 36 of the body which is directed in-wardly relative to the maximum interior wall radius of the device. The minimum diameter of the hour-glass shape 36 can be positioned approximately 2.25 inches from the outside front end (e.g., second opening 28) of the device. The extent of the hour-glass shape 36 can be approximately 1.5 inches in length. Another similar (half) hour-glass shaped restriction can be designed to be very near the largest opening (e.g., first opening 26) of the device.

Dimensions and Tolerances: Final overall outside diameters and lengths may be within +/−0.050 inches of the desired values listed in "parts." Tubular wall thickness may be within +/−0.005 inches of design drawing values. Snap fit diameters can be within +/−0.0005 inches.

Compatibility With Oils and Solvents

The composition material can be selected such that its appearance and/or functionality is not substantially altered by exposure to: typical household cleaning solutions such as water, soapy water, rubbing alcohol, orange peel oil based solvents. Also, material of construction may withstand being soaked and/or covered with lotions and creams typically used in personal skin softening and massaging (e.g., petroleum jelly, hand/body lotions, etc.).

Sterilization and Cleaning:

The erectile aid plastic device may be capable of sterilization by, for example, standard medical autoclaving. The plastic of construction may also withstand typical kitchen dish washer cycles and cleaning soaps.

Strength and Durability

The erectile aid may be strong enough to not crack or break during normal use. For example, a single hand squeeze by a human should not permanently deform the body of the device's tubular structure. Typical hand squeezing pressures (or forces of approximately 25 lbs) should not be able to exceed the elastic limits of the material of construction nor permanently deform the natural molded tubular shape of the device. The erectile aid should not collapse when a partial vacuum of approximately −5 PSI below ambient is drawn on its interior. The erectile aid should not crack or break (e.g., disrupting its ability to function as a partial vacuum) after being dropped onto a floor from a height of approximately 5 Feet.

Operable Temperature Range

The erectile aid may be able to withstand and be fully functional after exposure to temperatures ranging from −30 degrees F. (e.g., possible car storage temperatures during a cold winter) to +220 degrees F. (e.g., scalding water used for cleaning)

Dimensions of Openings:

One end of the erectile aid (and specifically, the vessel) may contain a concentric opening of approximately 0.250 inches in diameter. This opening can receive (or be covered with) a snap fit integral cap cover which includes a one-way essentially flat flapper valve and seal mechanism. The opening at the opposite end may be nearly the full diameter of the tubular structure but have a radius of curvature at about the inner wall radius of the tube. This opening can be smooth and polished in nature and free of any rough obtrusions above the normal radii of curvature. Raised molding seam line flashing in this region can be minimal and/or removed, and this region can be buffed to a fine finish for the purpose of the products appearance and use.

Snap Fit Circular Radius on Small Opening End

The small opening end of the erectile aid may include a snap-fit circular lip on its outer periphery. The front face of the device may be flat inside the peripheral lip. The small opening in the unit may be concentric to the body of the device. The protrusion in the dome end of the main body of the device may hold and maintain a tight fitting thin plastic snap-on integral cap cover which includes a one-way flapper valve and/or seal mechanism which resembles a miniature open cupped flying disc in shape and design.

Stiffness of the Body of Erectile Aid

Typically ridged—in plastic e.g., hardness of 80 on the "Shore A" elastomeric scale or higher (e.g., 85, 90, or higher and up)

Stiffness of the Cap Seal of Erectile Aid

Typically ridged—made of plastic e.g., of "Shore A" hardness of approximately 80 or lower (e.g., 65, 55, or possibly as low as "Shore A" 35).

The end cap seal may provide a flapper valve design which creates an automatic partial vacuum within the erectile aid during (and after) normal reciprocal motion use. The end-cap may be a non-protruding design. The end-cap may allow for easy removal, via, e.g., placement of a fingernail around and/or under any portion of the outer most edge of the end-cap periphery, and lifting the outer periphery edge away from the body of the erectile aid. Doing so may break any vacuum contained within the device. Otherwise, the end-cap may remain securely fastened during use. Security of fastening may be provided using one or more approaches. For example, the internal vacuum created within the device can hold the end-cap in place, due to the outside atmospheric pressure exceeding the internal lower pressure. Further, the rim of the end-cap can be designed to snap and hold securely the end-cap in place around the protruding ridge (lip) which is molded into the top end (TE section, FIG. 7) of the erectile aid.

The end-cap seal may provide a solution for the user to quickly break any partial vacuum which has previously been generated and/or held within the interior of the erectile aid. By placing one's finger-nail in the opening of the end cap slot and lifting upward on the flap, any partial vacuum which exists within the vessel can be released.

Thickness of Erectile Aid (Material)

In general, the thickness of the erectile aid may be constant throughout the whole shape, except near the extreme open end and/or just under the valve/seal-cap portion of the device. The thickness of any particular design of the erectile aid could range from 1/10 to 1/50 of the actual inside diameter of the device. The thickness of the device may depend upon material choice. Stronger materials may allow a thinner walled design, whereas weaker materials of construction may have thicker walls of construction. Because the inside diameters of these erectile aids can range from approximately 1.3 inches to over approximately two (2) inches, the thickness of a manufactured device could be anywhere from just a few mils (one "mil" being 1/1000 of an inch), e.g., 30 mils, if it were made out a strong material like metal, to approximately 2/10 of an inch in thickness if it were made out of a plastic.

Thickness of the Device Under the End-Cap Seal

The thickness of the device may be slightly thinner under the center of the end-cap seal. The wall thinning may allow the protrusion of the cap-seal to be minimized. The flat region which partially cuts off a portion of the end tip wall thickness of the crown portion of the TE section (or, prolate ellipsoid shell) also provides for the use of a simple flat-shaped flap, to seal (or unseal) the interior of the device during use through the vessel's second opening.

Thickness of the Device Around the Extreme Far End of the (OE) Section

This portion may be shaped somewhat like a donut. The restricting inside diameter and the thick radius of the opening curvature is designed to reduce and/or minimize the pressure that the device could apply to the user in the region of and around the base of the user's penis. Typically, the vessel's opening donut cross-sectional shape may be about 0.30 to 0.60 inches in thickness. Depending upon how the donut shape of the opening is formed, the opening may provide a contacting radius of curvature slightly greater than the wall thicknesses of the other portions of the vessel.

Open Hole Under the End-Cap Seal

In one embodiment of the end-cap seal there is an axisymmetric hole under the center of the end-cap seal. The diameter of this hole may range from approximately 1/16 to 3/10 of an inch in diameter. The exact dimension of this hole may be determined by the end-cap seal thickness and the stiffness of the "flap" portion of the end-cap valve/seal, which creates the seal over the top end hole (second opening) in the device. Smaller second opening holes may be used with thinner and/or more flexible end cap seal covers. Conversely, larger second openings may be needed if used with thicker less flexible end cap seal covers.

Section (TE)

The Top End (TE) may be one-half of a hollowed-out prolate ellipsoid. A hollowed-out prolate ellipsoid is similar to the shell of a pointy egg-shaped object.

Section (HG)

The Hour Glass (HG) section may look substantially like a regular hour-glass except that it has a very shallow minimal diameter. The minimum diameter of the inner surface of this section may be approximately 85% of the inner diameter of the (CT) Section. This ratio may hold for all production sizes of the erectile aid device. The minimum diameter of the Open End (OE) section has a similar design ratio over all sizes.

HG section may aid in providing a continuous application of increased tractive (tractal) forces on the outer surface of a penis when the penis is inserted and expanded through the application of a partial vacuum created within the erectile aid. The repeated application of tractive (tractal) forces on any available foreskin of a penis will ultimately (over time, e.g., one to three years) expand the length of the available foreskin to the approximate length it was before it was circumcised. This function is provided quite readily with the present design of the erectile aid.

Cylindrical Tube (CT) Section

The constant diameter and cylindrical design of this tubular CT structure may provide a simple way to expand or contract the overall length of the erectile aid during production.

Open End (OE) Section

Single versus Multiple Section Designs—the present erectile aid may be produced as a single-piece device, except for the addition of the separate end-cap. It is possible that snap joints may be employed between any of the four major sections of the erectile aid described herein. For example, a joint might be very desirable between the HG and CT sections. A snap joint between the sections in the design may provide for easy lubricating, cleaning, storage, and travel.

Non-Exhaustive List of Potential Benefits

To remedy erectile dysfunction with successful therapeutic treatments utilizing the automatic partial vacuum creating design.

To provide a convenient method for un-circumcising adult males through the application of repetitive periodic tractive (tractal) forces on available circumcised foreskin.

To reduce dependency on pharmaceutical methods of treating erectile dysfunction.

To reduce or offset the debilitating impact some diseases (for example, diabetes) have on producing ED.

To raise the level of satisfaction of the normal sex experience through personal, private, and intimate self and/or partner assisted manipulation techniques. The tractal device is considered as a temporary erectile generating aid for use during the prelude to a normal sex experience and may be removed just prior to copulation.

To learn to expand and prolong the pleasurable experience of normal sex through personal, private, and intimate self and/or partner assisted manipulation techniques. The tractal device is considered as a temporary erectile generating aid for use during the prelude to a normal sex experience and may be removed just prior to copulation.

Example Embodiments Including Seal Cap With Support Member

In another embodiment, the arcuate or semi-circular slit in the seal cap can be divided by one or more support member(s) (which can also be referred to as a "bridge"). The support members(s) can divide the arcuate or semicircular slit into two or more sections (e.g., arcs). The support member(s) can help to support the seal cap, and prevent bending or curling of the seal cap. Maintaining the structural integrity of the seal cap can help to provide an effective seal over the one-way valve, thereby enhancing the performance of the device.

Figure 16:
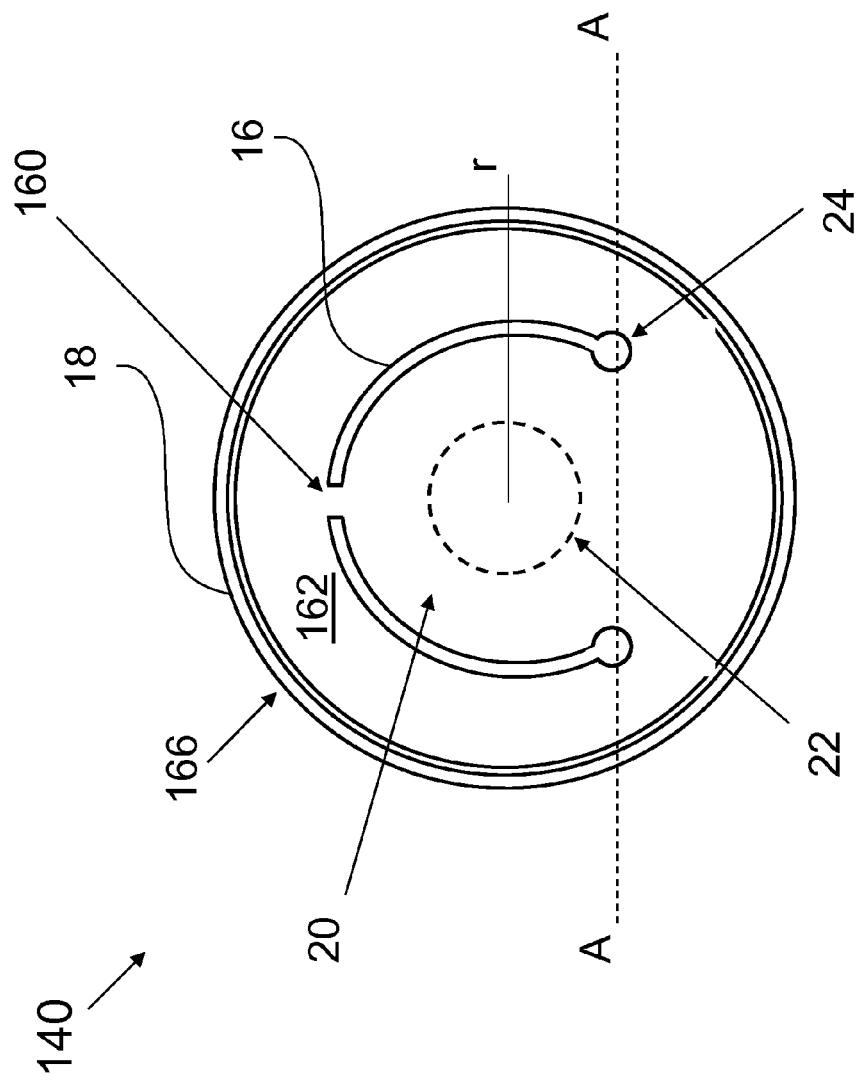
FIG. 16 shows an axial inner view of an alternative embodiment of a cap member according to various embodiments.
Figure 17:
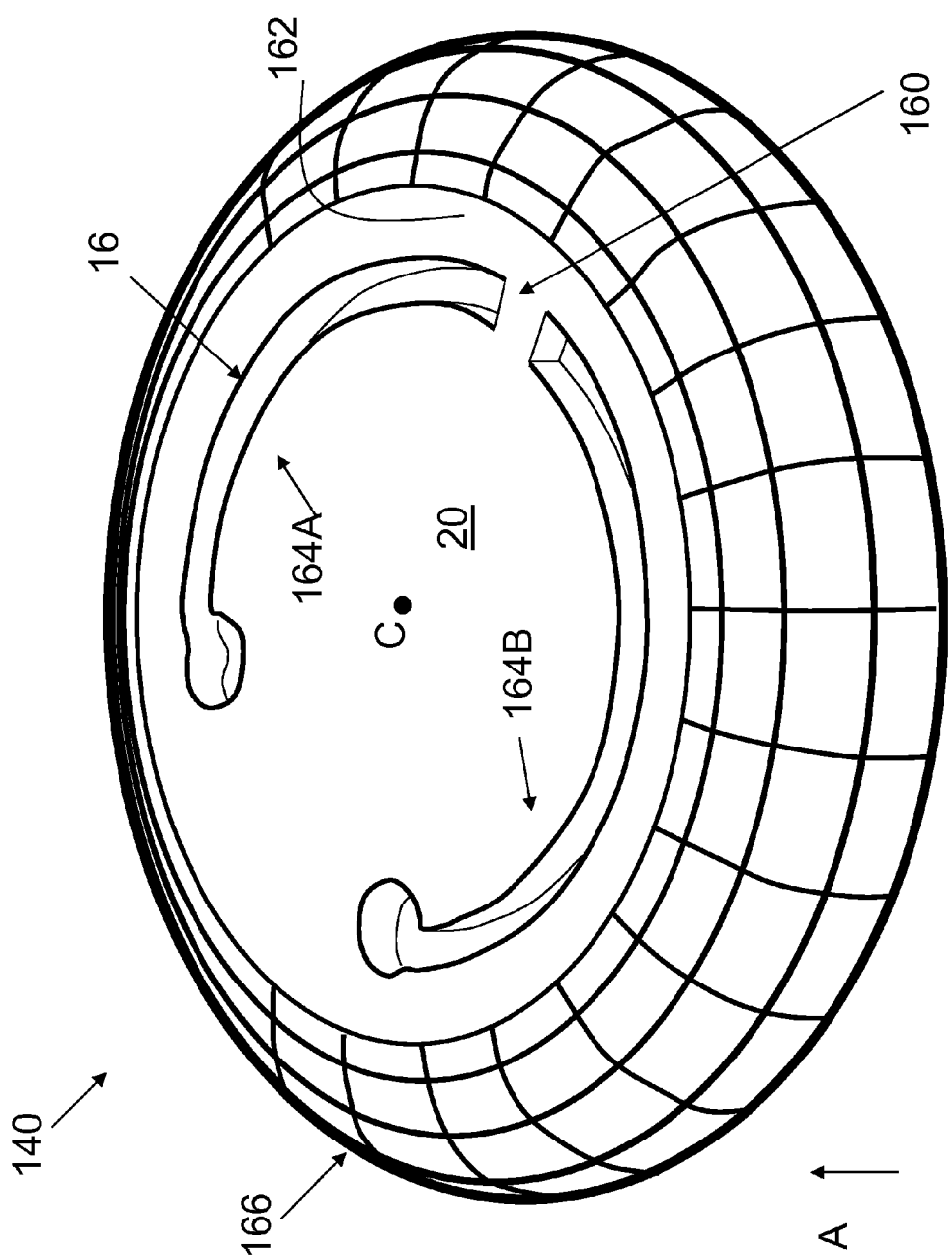
FIG. 17 shows a three-dimensional perspective view from a top of the cap member of FIG. 16.

FIGS. 16-17 illustrate the use of the support member in conjunction with embodiments described herein.

FIG. 16 shows an axial inner view of an alternative embodiment of a cap member 140 according to various embodiments. FIG. 17 shows a three-dimensional perspective view from a top of the cap member 140. The cap member 14 can include a support member 160 spanning between a movably attached portion 20 and a fixed rim portion 162. That is, the support member 160 can substantially affix the movably attached portion 20 to the fixed rim portion 162, thereby limiting the movement of the movably attached portion 20 relative to the remainder of the cap member 140. In other words, the seal cap 140 includes a support member 160 spanning a width of the arcuate or semi-circular slit 16. That is, the support member 160 can span between the movably attached portion 20 (e.g., flap portion) of the seal cap 140 and the fixed portion (fixed rim portion 162) of the seal cap 140.

As noted herein, the support member(s) 160 can divide the slit 16 between the flap (movably attached portion 20) and the fixed portion (fixed rim portion 162) of the seal cap 140 into two or more sections. In some cases, as shown in FIG. 17, one support member 162 divides the slit into two equally sized arcuate sections, 164A and 164B. In other cases, one support member divides the slit into two unevenly sized arcuate sections. In still other cases, a plurality of support members (e.g., two or more) divide the slit into three or more arcuate sections. These three or more sections can be approximately equally sized in some cases.

In various embodiments, the support member at least partially retains the seal cap in an axial direction (A) of the vessel.

In various other embodiments, the support member 160 spans an axial length of the seal cap 140. That is, in some embodiments, the support member 160 can have a thickness substantially equal to the thickness of the seal cap 140 at the junction of the flap (movably attached portion 20) and the support member 160 (e.g., as measured along axial direction A). In some other embodiments, the support member is thinned or tapered in thickness from an outer edge 166 of the seal cap 140 towards an axial center (C) of the seal cap.

In some cases, the support member 160 stiffens and secures the center portion of the full arc "c-shaped" (arcuate or semi-circular) cut-out of the cap seal flap (movably attached portion 20). The support member 160 minimizes the curling tendency of the otherwise flexible rubber flap. If the flap (movably attached portion 20) curls during use, it may not provide an integral flexible (yet flat) seal cover over the small opening in the tractal erectile device. The bridge element (as shown in FIGS. 16-17) can help to improve the one-way sealing action utilized in conjunction with the small opening of the vessel. The small opening of the tractal erectile device lies directly under, and at the center of the "c-shape" of the seal cap which is displayed in FIG. 17 from a top perspective view.

Figure 18:
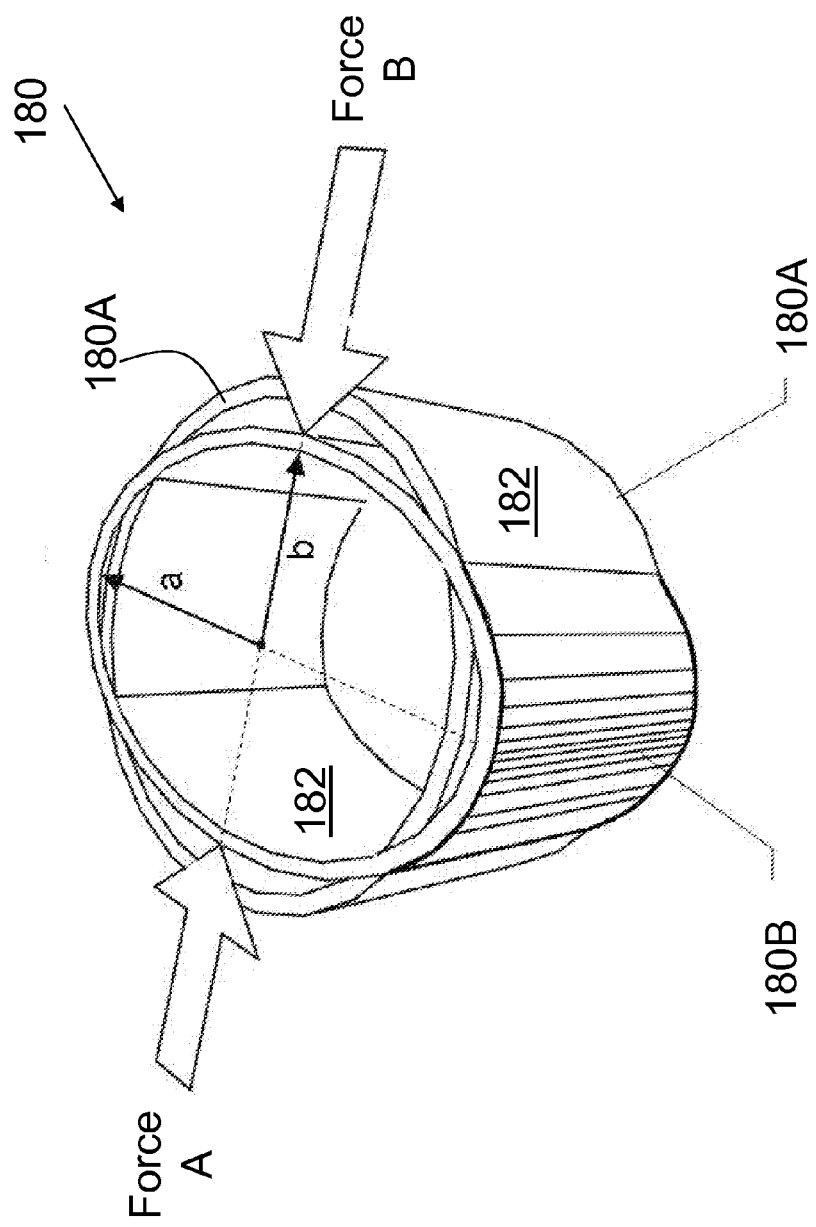
FIG. 18 shows a schematic axial cut-away view of a portion of an erectile aid at rest, and in compression, according to various embodiments.

FIG. 18 shows a schematic axial cut-away view of a portion of an erectile aid (e.g., erectile aid 10) at rest, and in compression, according to various embodiments. This may include, e.g., a section 180 taken from the lip portion (e.g., lip portion 32, FIG. 6), elongated portion (e.g., elongated portion 34, FIG. 6) or hour-glass portion (e.g., hour-glass portion 36, FIG. 6) of any erectile aid shown and/or described herein. In a particular embodiment, the section 180 is part of the elongated portion 34 of an erectile aid. In various embodiments, the erectile aides shown and described herein can be formed of a deformable material. That is, the erectile aid shown and described according to various embodiments can be formed of a material that is compressible in response to an applied external force, e.g., the force of a human hand. FIG. 18 illustrates deformation of the section 180, e.g., via one or more opposing forces (Force A/Force B). Section 180 is shown at rest, without applied forces, as 180A; and under pressure (from Force A/Force B) as 180B. Force A and/or Force B could be applied, e.g., by a human operator such as a human hand. Force A and/or Force B can cause compression of the walls 182 of the section 180, causing movement of air within the erectile aid (e.g., creating an internal vacuum condition).

Figure 19:
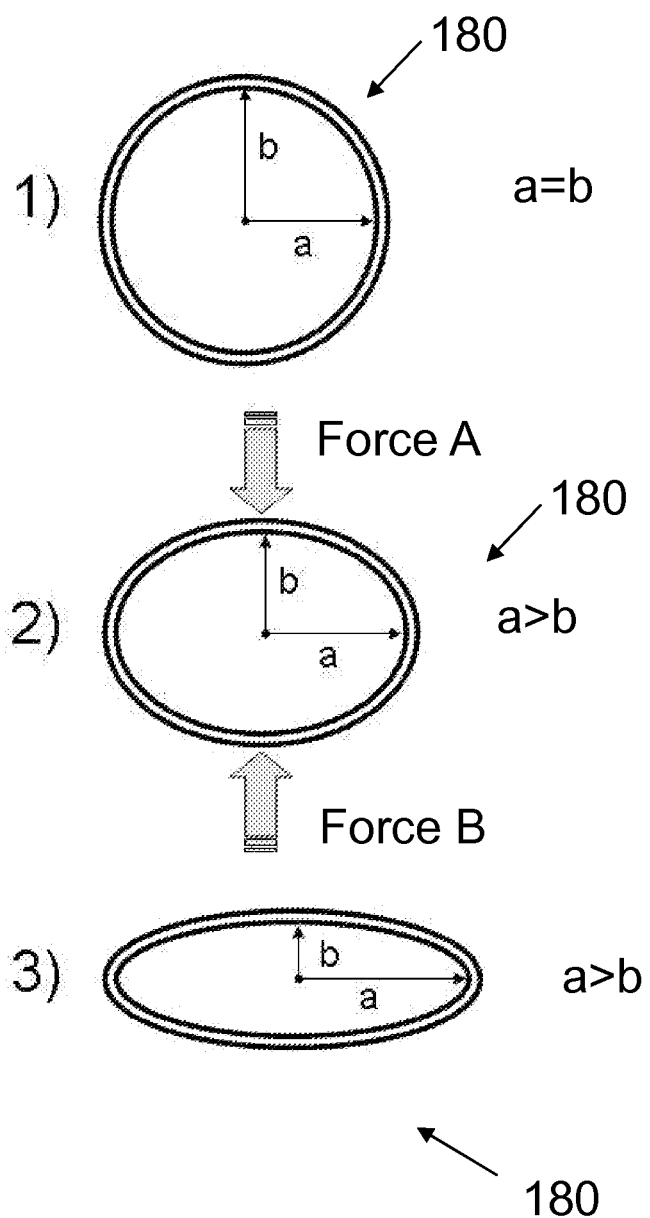
FIG. 19 shows a schematic axial cross-sectional view of the section of an erectile aid in FIG. 18, in three phases of contraction, according to various embodiments.

FIG. 19 shows a schematic axial cross-sectional view of the section 180 of FIG. 18 in three phases of contraction: 1) Without an applied external force; 2) During application of external forces (Force A and Force B); and 3) Resulting deformation from continued increase in external forces (Force A and Force B).

FIG. 20 shows an example table (Table 2) illustrating the relative partial vacuum effect of deformation and release of the walls 182 of section 180. Table 2 illustrates the relationship between percentage of sidewall deflection (of radius, b, in FIG. 19) and the internal pressure within the erectile aid. The example data in Table 2 also shows the force applied (in pounds-force, lbs) to the walls 182 to cause the corresponding deflection and pressure change.

With reference to FIGS. 18-20, it is understood that deformation of the walls (e.g., walls 182) of the erectile aid can cause an increase in pressure within the chamber of the erectile aid. That is, as the walls are deformed, e.g., due to compressive force, the air within the chamber will increase in pressure and exert a force on the seal cap. When that internal pressure on the seal cap exceeds the cap's resistive force (e.g., based upon its weight and coefficient of friction), the cap is displaced and air is released from the chamber. As described herein, once that internal pressure force drops below the cap's resistive force, the cap returns to its resting position, sealing the chamber and creating the vacuum effect. It is understood that this vacuum effect is enhanced by the seal between the human organ and the walls (e.g., walls 182) of the chamber. In some cases, when compressing the erectile aid, the organ will similarly compress/displace with the movement of the wall, maintaining the effective seal of the chamber proximate the lip portion (e.g., lip portion 32). In various embodiments, the walls of the chamber can be formed of a material (and with a thickness and radius of curvature) that has a similar elasticity to the human organ (e.g., human penis).

In various embodiments, the elastomeric material that forms the walls (e.g., walls 182) of the erectile aid can have enough internal compressiveness to be able to quickly (e.g., within fractions of a second) return to its original shape, e.g., after compression by an operator (such as by the hand of a human operator). In various embodiments, at least the walls (e.g., walls 182) can be formed of a thermoplastic urethane material having a shore hardness within ranges described according to the various embodiments. In some cases, the walls may have a thickness between approximately 0.10 inches and approximately 0.25 inches. In some embodiments, the cross-sectional diameter of the section 180 (including walls 182) can range from approximately 1.50 inches to approximately 3.00 inches.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A device comprising:
   a vessel having a first opening for receiving an organ, and a second opening for releasing fluid from within the vessel, the vessel including:
   a lip portion surrounding the first opening;
   an elongated portion connected to the lip portion;
   an hour-glass portion connected to the elongated portion; and
   an end portion including the second opening;
   a seal cap including an integral one-way valve fluidly connected to the second opening, the integral one-way valve allowing for release of fluid from within the vessel,
   wherein the seal cap includes an arcuate or semi-circular slit for allowing the fluid to release from within the vessel to ambient,
   wherein the seal cap includes a support member spanning a width of the arcuate or semi-circular slit, wherein the support member at least partially retains the seal cap in an axial direction of the vessel.

2. The device of claim 1, further comprising a one-way valve fluidly connected to the second opening, the one-way valve allowing for release of the fluid from within the vessel.

3. The device of claim 2, further comprising a seal cap connected to the one-way valve, wherein the seal cap includes an arcuate or semi-circular slit for allowing the fluid to release from within the vessel to ambient.

4. The device of claim 3, wherein the arcuate or semi-circular slit is fluidly connected to at least one of a bulbous, a rounded or an expanded opening extending along an axis of the seal cap.

5. The device of claim 4, wherein the at least one of the bulbous, rounded, or expanded opening increases the useable lifespan of the seal cap as it undergoes repeated movement due to the release of the fluid from the vessel.

6. The device of claim 4, wherein the release of the fluid from the vessel produces a partial vacuum within the vessel during reciprocal motion use.

7. The device of claim 3, wherein the semi-circular slit extends between approximately 270 degrees and approximately 330 degrees along a circle having a central axis being coaxial with a primary axis of the elongated portion.

8. The device of claim 3, further comprising a reinforcing member affixed to a surface of the seal cap between a center point of the seal cap and a portion of the semi-circular slit.

9. The device of claim 8, wherein the reinforcing member includes a protrusion extending from the surface of the seal cap.

10. A device comprising:
a vessel having a first opening for receiving an organ, and a second opening for releasing a fluid from within the vessel, the vessel including:
a lip portion surrounding the first opening;
an elongated portion connected to the lip portion;
an hour-glass portion connected to the elongated portion; and
an end portion including the second opening; and
a one-way valve fluidly connected to the second opening, the one-way valve allowing for release of the fluid from within the vessel; and
a seal cap connected to the one-way valve, the seal cap including a slit extending across an axial center of the seal cap,
wherein the seal cap includes a support member spanning a width of the arcuate or semi-circular slit, wherein the support member at least partially retains the seal cap in an axial direction of the vessel.

11. The device of claim 10, wherein the seal cap is substantially rounded, and wherein the slit extends from a first location along an outer edge of the seal cap to a second location along the outer edge of the seal cap.

12. The device of claim 10, wherein the slit includes a pair of bulbous ends.

13. The device of claim 12, wherein the pair of bulbous ends are located proximate a top surface of the seal cap.

14. The device of claim 13, wherein a distance from the pair of bulbous ends to the top surface of the seal cap is less than a distance from a second portion of the slit from the top surface of the seal cap.

15. A device comprising:
a vessel having a first opening for receiving an organ, and a second opening for releasing a fluid from within the vessel, the vessel including:
a lip portion surrounding the first opening;
an elongated portion connected to the lip portion;
an hour-glass portion connected to the elongated portion; and
an end portion including the second opening,
wherein at least two of the elongated portion, the hour-glass portion and the end portion are connected via complementary semi-circumferential tabs extending respectively, from the at least two of the elongated portion, the hourglass portion and the end portion; and
a seal cap including an integral one-way valve fluidly connected to the second opening, the integral one-way valve allowing for release of fluid from within the vessel,
wherein the seal cap is molded continuously with the vessel, the seal cap including an arcuate or semi-circular slit for allowing the fluid to release from within the vessel to ambient,
wherein the seal cap includes a support member spanning a width of the arcuate or semi-circular slit, wherein the support member at least partially retains the seal cap in an axial direction of the vessel.

16. The device of claim 15, wherein the support member spans an axial length of the seal cap measured along the axial direction of the vessel.

17. The device of claim 1, wherein the support member divides the arcuate or semi-circular slit into two or more sections.

18. The device of claim 10, wherein the support member has an axial thickness equal to an axial thickness of the seal cap at a junction of the movably attached portion and the support member.

* * * * *